(12) United States Patent
Perricone

(10) Patent No.: US 9,314,423 B2
(45) Date of Patent: *Apr. 19, 2016

(54) HAIR TREATMENT SYSTEMS AND METHODS USING PEPTIDES AND OTHER COMPOSITIONS

(71) Applicant: Transdermal Biotechnology, Inc., Meriden, CT (US)

(72) Inventor: Nicholas V. Perricone, Madison, CT (US)

(73) Assignee: Transdermal Biotechnology, Inc., Meriden, CT (US)

( * ) Notice: Subject to any disclaimer, the term of this patent is extended or adjusted under 35 U.S.C. 154(b) by 93 days.

This patent is subject to a terminal disclaimer.

(21) Appl. No.: 13/801,488

(22) Filed: Mar. 13, 2013

(65) Prior Publication Data

US 2014/0271810 A1    Sep. 18, 2014

(51) Int. Cl.
| | |
|---|---|
| A61K 9/127 | (2006.01) |
| A61K 9/00 | (2006.01) |
| A61K 33/00 | (2006.01) |
| A61K 38/06 | (2006.01) |
| A61L 2/00 | (2006.01) |
| A61L 9/00 | (2006.01) |

(52) U.S. Cl.
CPC ............ *A61K 9/0014* (2013.01); *A61K 33/00* (2013.01); *A61K 38/066* (2013.01); *A61L 2/00* (2013.01); *A61L 9/00* (2013.01)

(58) Field of Classification Search
None
See application file for complete search history.

(56) References Cited

U.S. PATENT DOCUMENTS

| | | |
|---|---|---|
| 4,174,296 A | 11/1979 | Kass |
| 4,333,927 A | 6/1982 | Ofuchi et al. |
| 4,614,730 A | 9/1986 | Hansen et al. |
| 4,624,665 A | 11/1986 | Nuwayser |
| 4,687,661 A | 8/1987 | Kikuchi et al. |
| 4,708,861 A | 11/1987 | Popescu et al. |
| 4,743,449 A | 5/1988 | Yoshida et al. |
| 4,866,038 A | 9/1989 | Hruby et al. |
| 5,120,561 A | 6/1992 | Silvia et al. |
| 5,151,272 A | 9/1992 | Engstrom et al. |
| 5,206,219 A | 4/1993 | Desai |
| 5,254,348 A | 10/1993 | Hoffmann et al. |
| 5,380,761 A | 1/1995 | Szabo et al. |
| 5,391,548 A | 2/1995 | Francoeur et al. |
| 5,434,136 A | 7/1995 | Mathias |
| 5,439,967 A | 8/1995 | Mathur |
| 5,446,025 A | 8/1995 | Lu et al. |
| 5,476,651 A | 12/1995 | Meybeck et al. |
| 5,484,816 A | 1/1996 | Yanagida et al. |
| 5,504,117 A | 4/1996 | Gorfine |
| 5,550,263 A | 8/1996 | Herslof et al. |
| 5,576,016 A | 11/1996 | Amselem et al. |
| 5,656,286 A | 8/1997 | Miranda et al. |
| 5,662,932 A | 9/1997 | Amselem et al. |
| 5,674,912 A | 10/1997 | Martin |
| 5,693,676 A | 12/1997 | Gorfine |
| 5,726,164 A | 3/1998 | Weder et al. |
| 5,753,259 A | 5/1998 | Engstrom et al. |
| 5,776,494 A | 7/1998 | Guskey et al. |
| 5,807,573 A | 9/1998 | Ljusberg-Wahren et al. |
| 5,814,666 A | 9/1998 | Green et al. |
| 5,858,398 A | 1/1999 | Cho |
| 5,869,539 A | 2/1999 | Garfield et al. |
| 5,874,479 A | 2/1999 | Martin |
| 5,879,690 A | 3/1999 | Perricone |
| 5,891,472 A | 4/1999 | Russell |
| 5,955,502 A | 9/1999 | Hansen et al. |
| 5,976,562 A | 11/1999 | Krall et al. |
| 5,985,298 A | 11/1999 | Brieva et al. |
| 6,022,561 A | 2/2000 | Carlsson et al. |
| 6,045,827 A | 4/2000 | Russell |
| 6,099,851 A | 8/2000 | Weisman et al. |
| 6,103,275 A | 8/2000 | Seitz et al. |
| 6,133,320 A | 10/2000 | Yallampalli et al. |

(Continued)

FOREIGN PATENT DOCUMENTS

| | | |
|---|---|---|
| CA | 2182390 A1 | 8/1995 |
| CA | 2181390 A1 | 1/1997 |

(Continued)

OTHER PUBLICATIONS

Gasper et al. (Thyrotropin releasing hormone; a new player in human hair-growth, The FASEB Journal .www.fasebj.org).*
International Search Report and Written Opinion for Application No. PCT/US2014/025574 mailed Jun. 23, 2014.
International Search Report and Written Opinion mailed Jul. 1, 2014 for PCT/US2014/025629.
International Search Report and Written Opinion mailed Jul. 2, 2014 for PCT/US2014/025707.
International Search Report and Written Opinion for Application No. PCT/US2014/025757 mailed Jun. 23, 2014.
Invitation to Pay Additional Fees mailed Jun. 30, 2014 for PCT/US2014/025822.

(Continued)

*Primary Examiner* — Snigdha Maewall
(74) *Attorney, Agent, or Firm* — Wolf, Greenfield & Sacks, P.C.

(57) ABSTRACT

The present invention generally relates to compositions and methods for transdermal delivery, and treatment of hair related conditions. The compositions can be used in a variety of applications, including causing or promoting hair growth and/or hair pigmentation. In some cases, the composition may include nitric oxide and/or peptides. The nitric oxide and/or peptide may be present within a first phase comprising a lecithin, such as phosphatidylcholine. In certain embodiments, the lecithin is present in liposomes, micelles, or other vesicles containing nitric oxide, peptides, or both. The composition can take the form of a gel, a cream, a lotion, an ointment, a solution, a solid "stick," etc., that can be rubbed or sprayed onto the skin, e.g., onto the scalp, or other suitable portion of the skin. Other aspects of the present invention are generally directed to methods of making or using such compositions, methods of promoting such compositions, kits including such compositions, or the like.

31 Claims, 1 Drawing Sheet

(56) References Cited

U.S. PATENT DOCUMENTS

| | | | |
|---|---|---|---|
| 6,165,500 A | 12/2000 | Cevc | |
| 6,191,121 B1 | 2/2001 | Perricone | |
| 6,193,997 B1 | 2/2001 | Modi | |
| 6,207,713 B1 | 3/2001 | Fossel | |
| 6,211,250 B1 | 4/2001 | Tomlinson et al. | |
| 6,214,375 B1 | 4/2001 | Modi | |
| 6,242,099 B1 | 6/2001 | Grandmontagne et al. | |
| 6,242,421 B1 | 6/2001 | Bowen | |
| 6,287,601 B1 | 9/2001 | Russell | |
| 6,294,192 B1 | 9/2001 | Patel et al. | |
| 6,391,869 B1 | 5/2002 | Parks et al. | |
| 6,458,841 B2 | 10/2002 | Fossel | |
| 6,464,987 B1 | 10/2002 | Fanara et al. | |
| 6,521,250 B2 | 2/2003 | Meconi et al. | |
| 6,538,061 B2 | 3/2003 | Chaiyawat et al. | |
| 6,555,573 B2 | 4/2003 | Rosenbloom | |
| 6,780,849 B2 | 8/2004 | Herrmann et al. | |
| 6,932,963 B2 | 8/2005 | Perricone | |
| 6,936,044 B2 | 8/2005 | McDaniel | |
| 7,033,574 B1 | 4/2006 | Schneider et al. | |
| 7,182,956 B2 | 2/2007 | Perricone et al. | |
| 7,189,761 B2 | 3/2007 | Gorfine | |
| 7,696,247 B2 | 4/2010 | Herrmann et al. | |
| 7,820,420 B2 | 10/2010 | Whitlock | |
| 7,976,743 B2 | 7/2011 | Huang et al. | |
| 8,273,711 B2 | 9/2012 | Perricone | |
| 8,435,942 B2 | 5/2013 | Perricone et al. | |
| 8,668,937 B2 | 3/2014 | Perricone et al. | |
| 8,871,254 B2 | 10/2014 | Perricone | |
| 8,871,255 B2 | 10/2014 | Perricone | |
| 8,871,256 B2 | 10/2014 | Perricone | |
| 8,871,257 B2 | 10/2014 | Perricone | |
| 8,871,258 B2 | 10/2014 | Perricone | |
| 8,871,259 B2 | 10/2014 | Perricone | |
| 8,871,260 B2 | 10/2014 | Perricone | |
| 8,871,261 B2 | 10/2014 | Perricone | |
| 8,871,262 B2 | 10/2014 | Perricone | |
| 9,050,248 B2 | 6/2015 | Perricone et al. | |
| 9,060,925 B2 | 6/2015 | Perricone et al. | |
| 2002/0082221 A1 | 6/2002 | Herrmann et al. | |
| 2002/0131994 A1 | 9/2002 | Schur et al. | |
| 2002/0153509 A1 | 10/2002 | Lynch et al. | |
| 2002/0160040 A1 | 10/2002 | Spicer et al. | |
| 2002/0182162 A1 | 12/2002 | Shahinpoor et al. | |
| 2004/0018237 A1* | 1/2004 | Perricone | 424/484 |
| 2004/0023878 A1 | 2/2004 | Arnold et al. | |
| 2004/0096494 A1* | 5/2004 | Siekmann et al. | 424/450 |
| 2004/0191305 A1 | 9/2004 | Perricone et al. | |
| 2004/0197391 A1 | 10/2004 | Perricone et al. | |
| 2005/0031651 A1 | 2/2005 | Gervais et al. | |
| 2005/0043245 A1 | 2/2005 | Siler-Khodr | |
| 2005/0074506 A1 | 4/2005 | Natan et al. | |
| 2005/0158309 A1 | 7/2005 | Levite et al. | |
| 2005/0226945 A1 | 10/2005 | Ruwart | |
| 2006/0058241 A1 | 3/2006 | Geier et al. | |
| 2006/0063703 A1 | 3/2006 | Prange et al. | |
| 2006/0105955 A1 | 5/2006 | Perricone | |
| 2006/0121115 A1 | 6/2006 | Leroux et al. | |
| 2006/0127469 A1 | 6/2006 | Perricone et al. | |
| 2006/0142186 A1 | 6/2006 | Gregory et al. | |
| 2006/0240116 A1 | 10/2006 | Jolley | |
| 2006/0275353 A1 | 12/2006 | Perricone et al. | |
| 2008/0153789 A1 | 6/2008 | Dmowski et al. | |
| 2008/0193385 A1 | 8/2008 | Maibach | |
| 2008/0249028 A1 | 10/2008 | Luo | |
| 2008/0311214 A1 | 12/2008 | Rao | |
| 2009/0214624 A1 | 8/2009 | Smith et al. | |
| 2009/0304815 A1 | 12/2009 | Cossu et al. | |
| 2009/0324698 A1 | 12/2009 | Wagner et al. | |
| 2010/0048520 A1 | 2/2010 | Safdi et al. | |
| 2010/0210568 A1* | 8/2010 | Bevec | 514/18 |
| 2010/0278784 A1 | 11/2010 | Pojasek et al. | |
| 2010/0286056 A1 | 11/2010 | Bohm | |
| 2010/0292139 A1 | 11/2010 | Perricone | |
| 2010/0292330 A1 | 11/2010 | Pan et al. | |
| 2010/0311696 A1 | 12/2010 | Perricone | |
| 2011/0020252 A1 | 1/2011 | Shantha et al. | |
| 2011/0104240 A1* | 5/2011 | Jones et al. | 424/443 |
| 2011/0123577 A1 | 5/2011 | Perricone et al. | |
| 2011/0130330 A1 | 6/2011 | Perricone | |
| 2011/0210568 A1 | 9/2011 | Bevec | |
| 2012/0156163 A1* | 6/2012 | Bauman et al. | 424/78.02 |
| 2013/0029989 A1 | 1/2013 | Coderre et al. | |
| 2013/0059017 A1 | 3/2013 | Perricone et al. | |
| 2014/0271730 A1 | 9/2014 | Perricone | |
| 2014/0271731 A1 | 9/2014 | Perricone | |
| 2014/0271732 A1 | 9/2014 | Perricone | |
| 2014/0271742 A1 | 9/2014 | Perricone | |
| 2014/0271743 A1 | 9/2014 | Perricone | |
| 2014/0271800 A1 | 9/2014 | Perricone | |
| 2014/0271801 A1 | 9/2014 | Perricone | |
| 2014/0271802 A1 | 9/2014 | Perricone | |
| 2014/0271803 A1 | 9/2014 | Perricone | |
| 2014/0271804 A1 | 9/2014 | Perricone | |
| 2014/0271805 A1 | 9/2014 | Perricone | |
| 2014/0271806 A1 | 9/2014 | Perricone | |
| 2014/0271807 A1 | 9/2014 | Perricone | |
| 2014/0271808 A1 | 9/2014 | Perricone | |
| 2014/0271809 A1 | 9/2014 | Perricone | |
| 2014/0271811 A1 | 9/2014 | Perricone | |
| 2014/0271934 A1 | 9/2014 | Perricone | |
| 2014/0271935 A1 | 9/2014 | Perricone | |
| 2014/0271936 A1 | 9/2014 | Perricone | |
| 2014/0271937 A1 | 9/2014 | Perricone | |
| 2014/0271938 A1 | 9/2014 | Perricone | |
| 2015/0004196 A1 | 1/2015 | Perricone | |
| 2015/0010521 A1 | 1/2015 | Perricone | |
| 2015/0010655 A1 | 1/2015 | Perricone | |
| 2015/0010656 A1 | 1/2015 | Perricone | |
| 2015/0010657 A1 | 1/2015 | Perricone | |
| 2015/0010658 A1 | 1/2015 | Perricone | |
| 2015/0010659 A1 | 1/2015 | Perricone | |
| 2015/0010660 A1 | 1/2015 | Perricone | |
| 2015/0010661 A1 | 1/2015 | Perricone | |
| 2015/0010662 A1 | 1/2015 | Perricone | |
| 2015/0216793 A9 | 8/2015 | Perricone | |
| 2015/0231053 A1 | 8/2015 | Perricone | |
| 2015/0231252 A1 | 8/2015 | Perricone | |
| 2015/0231253 A1 | 8/2015 | Perricone | |
| 2015/0238608 A1 | 8/2015 | Perricone et al. | |

FOREIGN PATENT DOCUMENTS

| | | |
|---|---|---|
| CN | 102 702 330 A | 10/2012 |
| EP | 0482554 A2 | 4/1992 |
| EP | 0561330 A1 | 9/1993 |
| EP | 0722323 A1 | 7/1996 |
| EP | 0727323 A1 | 8/1996 |
| EP | 0882736 A1 | 12/1998 |
| EP | 0995444 A2 | 4/2000 |
| EP | 1591128 A1 | 11/2005 |
| FR | 2 849 381 A1 | 7/2004 |
| JP | 60-58915 A | 4/1985 |
| JP | 60-155109 A | 8/1985 |
| JP | S63-502117 A | 8/1988 |
| JP | H05-502042 A | 4/1993 |
| JP | H05-51338 B2 | 8/1993 |
| JP | H06-316530 | 11/1994 |
| JP | 10-194994 A | 7/1998 |
| JP | 11-079975 | 3/1999 |
| JP | 2000-086501 | 3/2000 |
| JP | 2000-504033 A | 4/2000 |
| JP | 2001-500886 A | 1/2001 |
| JP | 2001-507689 A | 6/2001 |
| WO | WO 87/04592 A1 | 8/1987 |
| WO | WO 92/03122 A1 | 3/1992 |
| WO | WO 98/13025 A1 | 4/1998 |
| WO | WO 98/22090 A1 | 5/1998 |
| WO | WO 99/54358 A1 | 10/1999 |
| WO | WO 99/56725 A1 | 11/1999 |
| WO | WO 01/01963 A1 | 1/2001 |
| WO | WO 01/49268 A1 | 7/2001 |
| WO | WO 01/74377 A1 | 10/2001 |
| WO | WO 01/76537 A1 | 10/2001 |

(56) References Cited

FOREIGN PATENT DOCUMENTS

| WO | WO 02/05795 A2 | 1/2002 |
|---|---|---|
| WO | WO 02/19999 A2 | 3/2002 |
| WO | WO 02/30451 A1 | 4/2002 |
| WO | WO 02/064115 A1 | 8/2002 |
| WO | WO 02/064166 A1 | 8/2002 |
| WO | WO 03/101480 A1 | 12/2003 |
| WO | WO 2004/002440 A1 | 1/2004 |
| WO | WO 2004/060314 A2 | 7/2004 |
| WO | WO 2004/060315 A2 | 7/2004 |
| WO | WO 2005/023264 A1 | 3/2005 |
| WO | WO 2006/058318 A2 | 6/2006 |
| WO | WO 2006/097350 A1 | 9/2006 |
| WO | WO 2007/082726 A2 | 7/2007 |
| WO | WO 2008/013633 A2 | 1/2008 |
| WO | WO 2008/048514 A2 | 4/2008 |
| WO | WO 2009/033777 A1 | 3/2009 |
| WO | WO 2009/043529 A1 | 4/2009 |
| WO | WO 2009/046833 A1 | 4/2009 |
| WO | WO 2010/005687 A1 | 1/2010 |
| WO | WO 2011/117851 A1 | 9/2011 |
| WO | WO 2012/030716 A1 | 3/2012 |
| WO | WO 2012/125214 A1 | 9/2012 |
| WO | WO 2012/125241 A2 | 9/2012 |
| WO | WO 2013/127196 A1 | 9/2013 |
| WO | WO 2014/047153 A1 | 3/2014 |

OTHER PUBLICATIONS

Invitation to Pay Additional Fees mailed Jun. 30, 2014 for PCT/US2014/025913.
Invitation to Pay Additional Fees for Application No. PCT/US2014/025996 mailed Jun. 5, 2014.
International Search Report and Written Opinion mailed Jul. 25, 2014 for Application No. PCT/US2014/025996.
Invitation to Pay Additional Fees for Application No. PCT/US2014/025572 mailed Jun. 5, 2014.
Invitation to Pay Additional Fees mailed Jun. 30, 2014 for PCT/US2014/025630.
Invitation to Pay Additional Fees mailed Jul. 15, 2014 for PCT/US0214/025758.
Invitation to Pay Additional Fees mailed Jun. 30, 2014 for PCT/US2014/025898.
Invitation to Pay Additional Fees for Application No. PCT/US2014/025820 mailed Jun. 5, 2014.
International Search Report and Written Opinion mailed Jul. 25, 2014 for Application No. PCT/U52014/025820.
Invitation to Pay Additional Fees mailed Jun. 30, 2014 for PCT/US2014/025705.
Office Action mailed Apr. 9, 2014 for U.S. Appl. No. 13/801,518.
[No Author Listed] Database WPI, Week 201304; Thomson Scientific, London, GB; AN2013-A79457. XP002725745.
[No Author Listed] Dow Corning® 190 Fluid. Textile, Leather & Non-woven. Silicone-ethylene oxide/propylene oxide copolymer. 3 pages. Mar. 3, 2005.
[No Author Listed] Phospholipon® 80. Technical Data. American Lecithin Company. Copyright 2001-2011.
Brown et al. Skin pigmentation enhancers. Journal of Photochemistry and Photobiology B: Biology. Oct. 2001; 63(1-3):148-161.
Brunelli et al., Nitric oxide release combined with nonsteroidal antiinflammatory activity prevents muscular dystrophy pathology and enhances stem cell therapy. Proc Natl Acad Sci U S A. Jan. 2, 2007;104(1):264-9. Epub Dec. 20, 2006.
D'Amico et al. Luteinizing-hormone releasing hormone therapy and the risk of death from Alzheimer disease. Alzheimer Dis Assoc Disord. Jan.-Mar. 2010;24(1):85-9.
Dong et al. Nitric oxide enhances melanogenesis of alpaca skin melanocytes in vitro by activating the MITF phosphorylation. Molecular and Cellular Biochemistry. Mar. 23, 2011; 352(1-2):255-260.
Duong et al. Intracellular nitric oxide delivery from stable NO-polymeric nanoparticle carriers. Chem Commun. 2013; 49:4190-4192.

Freeman et al. Gonadotropin-releasing hormone agonist in treatment of premenstrual symptoms with and without comorbidity of depression: a pilot study. J Clin Psychiatry. May 1993;54(5):192-5.
Gaspar et al., Thyrotropin releasing hormone (TRH): a new player in human hair-growth control. FASEB J. Feb. 2010;24(2):393-403. doi: 10.1096/fj.08-126417. Epub Oct. 13, 2009.
Geier et al. A clinical trial of combined anti-androgen and anti-heavy metal therapy in autistic disorders. Neuroendocrinology Letters. Dec. 2006; 27(6):833-838.
Greydanus et al. Acne vulgaris and chronically ill adolescents. International Journal on Disability and Human Development. Jul. 2008; 7(3):319-327.
Holmes et al., Neuropeptide systems as novel therapeutic targets for depression and anxiety disorders. Trends in Pharmacological Sciences. Nov. 1, 2003; 24(11):580-588.
Huang et al., Transdermal iontrophoretic delivery of thyrotropin-releasing hormone across excised rabbit pinna skin. Drug Development. Jan. 1, 1996; 22(11):1075-1081.
Kakarla et al. A case of autoimmune progesterone dermatitis in an adolescent female. Journal of Pediatric and Adolescent Gynecology. Apr. 2006; 19(2):125-129.
Knuever et al., Thyrotropin-releasing hormone controls mitochondrial biology in human epidermis. J Clin Endocrinol Metab. Mar. 2012;97(3):978-86.
Lee et al. A case of autoimmune progesterone dermatitis misdiagnosed as allergic contact dermatitis. Allergy. Jan. 2011; 3(2):141.
Magnusson et al. Biological effects after percutaneous absorption of thyrotropin-releasing hormone and its analogue M-TRH. Peptides. Jan. 2001; 22(1):73-79.
Massol et al., Gonadotropin-releasing hormone (GnRH) as antidepressant: a psychopharmacological animal study. Science. Feb. 7, 1989; 160(3):395-399.
Schmidt et al. Hormone studies in females with androgenic hairloss. Gynecologic and Obstetric. 1991; 31(4):235-239.
Schmidt et al. Hyperprolactinemia and hypophyseal hypothyroidism as cofactors in hirsutism and androgen-inducded alopecia in women. Zeitschrift fur Dermatologie. Mar. 1991; 42(3):168-172.
Seabra, Nitric oxide-releasing nanomaterials and skin care. Chapter from Nanocosmetics and Nanomedicines. 2011:253-268.
Stojanovic et al. Endogenous estrogens increase postischemic hyperemia in the skin microcirculation. Journal of Cardiovascular Pharmacology. May 5, 2005; 45(5):414-417.
Yoon et al. Estrogen dermatitis responding to leuprolide acetate [2]. Journal of Dermatology. May 5, 2005; 32(5):405-406.
International Search Report and Written Opinion for Application No. PCT/US2012/000151 mailed Aug. 20, 2012.
Examiner's Report for Application No. AU 2003303517 mailed Dec. 1, 2006.
Canadian Office Action for Application No. CA 02511849 mailed May 8, 2009.
Canadian Office Action for Application No. CA 02511849 mailed Feb. 8, 2011.
Canadian Office Action for Application No. CA 02511849 mailed Sep. 14, 2011.
Chinese Office Action for Application No. CN 200380108020.0 mailed Jan. 19, 2007.
Chinese Office Action for Application No. CN 200380108020.0 mailed Aug. 3, 2007.
Chinese Office Action for Application No. CN 200380108020.0 mailed Mar. 14, 2008.
Chinese Office Action for Application No. CN 200380108020.0 mailed Nov. 28, 2008.
Chinese Office Action for Application No. CN 200380108020.0 mailed Mar. 6, 2009.
European Communication for Application No. EP 03815011.6 mailed Aug. 11, 2005.
Supplementary European Search Report for Application No. EP 03815011.6 mailed Aug. 16, 2006.
European Communication for Application No. EP 03815011.6 mailed Dec. 15, 2008.
Summons to Attend Oral Proceedings for Application No. EP 03815011.6 mailed Mar. 31, 2010.

(56) References Cited

OTHER PUBLICATIONS

Japanese Office Action for Application No. JP 2004-565850 mailed Mar. 24, 2009.
Japanese Office Action for Application No. JP 2004-565850 mailed Nov. 4, 2009.
Japanese Office Action for Application No. JP 2004-565850 mailed Aug. 2, 2011.
Japanese Office Action for Application No. JP 2004-565850 mailed Aug. 21, 2012.
Japanese Office Action for Application No. JP 2004-565850 mailed Mar. 5, 2013.
Korean Office Action for Application No. KR 10-2005-7012203 mailed Sep. 27, 2006.
Korean Office Action for Application No. KR 10-2005-7012203 mailed Jan. 25, 2007.
Korean Office Action for Application No. KR 10-2005-7012203 mailed Jun. 4, 2007.
Summary of Office Action issued in 2008 for MX PA/a/2005/007023.
International Search Report for Application No. PCT/US2003/041671 mailed Aug. 5, 2004.
Written Opinion for Application No. PCT/US2003/041671 mailed Oct. 21, 2004.
International Preliminary Report on Patentability for Application No. PCT/US2003/041671 completed Jan. 4, 2005.
Canadian Office Action for Application No. CA 2487305 mailed Nov. 5, 2008.
Canadian Office Action for Application No. CA 2487305 mailed Aug. 6, 2010.
Chinese Office Action for Application No. CN 03818027.8 mailed Jun. 9, 2006.
Chinese Office Action for Application No. CN 03818027.8 mailed Mar. 9, 2007.
Chinese Office Action for Application No. CN 03818027.8 mailed Aug. 20, 2007.
Chinese Office Action for Application No. CN 03818027.8 mailed Sep. 26, 2008.
Supplementary European Search Report for Application No. EP 03756329.3 mailed May 26, 2009.
Examination Report for for Application No. EP 03756329.3 mailed Apr. 6, 2010.
Examination Report for for Application No. EP 03756329.3 mailed Jul. 8, 2013.
Israeli Office Action for Application No. IL 165480 mailed Apr. 7, 2008.
Israeli Office Action for Application No. IL 165480 mailed May 6, 2009.
Japanese Office Action for Application No. JP 2004-508835 mailed Sep. 30, 2008.
Japanese Office Action for Application No. JP 2004-508835 mailed Feb. 16, 2010.
Japanese Office Action for Application No. JP 2004-508835 mailed Aug. 17, 2010.
International Search Report for PCT/US2003/017220 mailed Sep. 8, 2003.
International Preliminary Report on Patentability for Application No. PCT/US2003/017220 completed Feb. 22, 2004.
Office Action mailed Feb. 6, 2013 for U.S. Appl. No. 13/697,213.
Office Action mailed Mar. 25, 2013 for U.S. Appl. No. 13/697,213.
Office Action mailed Jul. 19, 2013 for U.S. Appl. No. 13/801,005.
Office Action mailed Jul. 19, 2013 for U.S. Appl. No. 13/801,075.
Office Action mailed Jul. 19, 2013 for U.S. Appl. No. 13/801,368.
Office Action mailed Jul. 1, 2013 for U.S. Appl. No. 13/801,429.
Office Action mailed Jul. 17, 2013 for U.S. Appl. No. 13/801,313.
Office Action mailed Jul. 19, 2013 for U.S. Appl. No. 13/801,373.
Office Action mailed Apr. 3, 2007 for U.S. Appl. No. 10/750,390.
Office Action mailed Aug. 28, 2007 for U.S. Appl. No. 10/750,390.
Office Action mailed Feb. 7, 2008 for U.S. Appl. No. 10/750,390.
Office Action mailed Aug. 20, 2008 for U.S. Appl. No. 10/750,390.
Appeal Brief mailed Jun. 23, 2009 for U.S. Appl. No. 10/750,390.
Appeal Brief mailed Jul. 21, 2009 for U.S. Appl. No. 10/750,390.
Supplemental Appeal Brief mailed Aug. 27, 2009 for U.S. Appl. No. 10/750,390.
Examiner's Answer to Appeal Brief mailed Nov. 10, 2009 for U.S. Appl. No. 10/750,390.
Reply Brief mailed Jan. 11, 2010 for U.S. Appl. No. 10/750,390.
Office Action mailed Sep. 7, 2011 for U.S. Appl. No. 10/750,390.
Office Action mailed May 10, 2012 for U.S. Appl. No. 10/750,390.
Appeal Brief mailed Dec. 11, 2012 for U.S. Appl. No. 10/750,390.
Office Action mailed Sep. 7, 2005 for U.S. Appl. No. 10/749,914.
Office Action mailed Apr. 17, 2006 for U.S. Appl. No. 10/749,914.
Office Action mailed Aug. 7, 2006 for U.S. Appl. No. 11/344,442.
Office Action mailed Mar. 6, 2007 for U.S. Appl. No. 11/344,442.
Office Action mailed Aug. 30, 2007 for U.S. Appl. No. 11/344,442.
Office Action mailed Feb. 7, 2008 for U.S. Appl. No. 11/344,442.
Appeal Brief mailed Jul. 3, 2008 for U.S. Appl. No. 11/344,442.
Examiner's Answer to Appeal Brief mailed Sep. 19, 2008 for U.S. Appl. No. 11/344,442.
Reply Brief and Appeal Brief mailed May 8, 2009 for U.S. Appl. No. 11/344,442.
Appeal Brief mailed May 20, 2009 for U.S. Appl. No. 11/344,442.
Miscellaneous Action with SSP mailed Jun. 4, 2010 for U.S. Appl. No. 11/344,442.
Office Action mailed Sep. 1, 2010 for U.S. Appl. No. 11/344,442.
Office Action mailed Feb. 27, 2008 for U.S. Appl. No. 11/506,137.
Office Action mailed Oct. 17, 2008 for U.S. Appl. No. 11/506,137.
Appeal Brief mailed Jul. 20, 2009 for U.S. Appl. No. 11/506,137.
Examiner's Answer to Appeal Brief mailed Nov. 3, 2009 for U.S. Appl. No. 11/506,137.
Reply Brief mailed Jan. 4, 2010 for U.S. Appl. No. 11/506,137.
Miscellaneous Action with SSP mailed Jun. 13, 2011 for U.S. Appl. No. 11/506,137.
Decision on Appeal mailed May 26, 2011 for U.S. Appl. No. 11/506,137.
Office Action mailed Jun. 4, 2013 for U.S. Appl. No. 11/506,137.
Office Action mailed Jul. 21, 2011 for U.S. Appl. No. 13/019,101.
Office Action mailed Feb. 13, 2012 for U.S. Appl. No. 13/019,101.
Office Action mailed Jun. 18, 2013 for U.S. Appl. No. 13/019,101.
Office Action mailed Aug. 11, 2005 for U.S. Appl. No. 10/448,632.
Office Action mailed Apr. 14, 2006 for U.S. Appl. No. 10/448,632.
Office Action mailed Nov. 1, 2006 for U.S. Appl. No. 10/448,632.
Appeal Brief mailed Mar. 30, 2007 for U.S. Appl. No. 10/448,632.
Office Action mailed Oct. 5, 2007 for U.S. Appl. No. 10/448,632.
Office Action mailed Jun. 17, 2008 for U.S. Appl. No. 10/448,632.
Office Action mailed Mar. 18, 2009 for U.S. Appl. No. 10/448,632.
Office Action mailed Nov. 4, 2009 for U.S. Appl. No. 10/448,632.
Appeal Brief mailed Sep. 6, 2010 for U.S. Appl. No. 10/448,632.
Examiner's Answer to Appeal Brief mailed Nov. 23, 2010 for U.S. Appl. No. 10/448,632.
Reply Brief mailed Jan. 24, 2011 for U.S. Appl. No. 10/448,632.
Decision on Appeal mailed Sep. 18, 2012 for U.S. Appl. No. 10/448,632.
Office Action mailed Apr. 16, 2013 for U.S. Appl. No. 10/448,632.
Office Action mailed Aug. 7, 2006 for U.S. Appl. No. 11/334,206.
Office Action mailed Mar. 6, 2007 for U.S. Appl. No. 11/334,206.
Office Action mailed Aug. 30, 2007 for U.S. Appl. No. 11/334,206.
Office Action mailed Jan. 24, 2008 for U.S. Appl. No. 11/334,206.
Appeal Brief mailed Jul. 14, 2008 for U.S. Appl. No. 11/334,206.
Examiner's Answer to Appeal Brief mailed Oct. 30, 2008 for U.S. Appl. No. 11/334,206.
Reply Brief mailed Dec. 30, 2008 for U.S. Appl. No. 11/334,206.
Reply Brief mailed May 8, 2009 for U.S. Appl. No. 11/334,206.
Miscellaneous Action with SSP mailed Jun. 4, 2010 for U.S. Appl. No. 11/334,206.
Office Action mailed Sep. 10, 2010 for U.S. Appl. No. 11/334,206.
Office Action mailed Apr. 19, 2011 for U.S. Appl. No. 11/334,206.
Office Action mailed Nov. 24, 2010 for U.S. Appl. No. 12/830,857.
Office Action mailed Jun. 10, 2011 for U.S. Appl. No. 12/830,857.
Office Action mailed Apr. 12, 2011 for U.S. Appl. No. 13/024,689.
Office Action mailed Jul. 21, 2011 for U.S. Appl. No. 13/024,689.
Office Action mailed Feb. 10, 2012 for U.S. Appl. No. 13/024,689.
Notice of Allowance mailed May 25, 2012 for U.S. Appl. No. 13/024,689.
Office Action mailed Nov. 4, 2010 for U.S. Appl. No. 12/796,213.

(56) References Cited

OTHER PUBLICATIONS

Office Action mailed Apr. 14, 2011 for U.S. Appl. No. 12/796,213.
[No Author Listed] About Soy Phospholipids. American Lecithin Company. Copyright 2000-2003. Last accessed online via http://www.americanlecithin.com/aboutphos.html on Sep. 29, 2007. 2 pages. (The year of publication is sufficiently earlier than the effective U.S. filing date and any foreign priority date so that the particular month of publication is not in issue. See MPEP 609.04(a)).
[No Author Listed] Dow Corning MSDS Dow corning 200 fluid 5 cst. Material Safety Data Sheet. Version 1.3. Revision date Apr. 21, 2008. 8 pages.
[No Author Listed] Dow Corning Product Information: 200® Fluid Fluid 50cs, 100cs, 200cs, 350cs, 500cs, 1000cs. Ref. No. 25-991B-01. Dated Oct. 11, 2000. 4 pages.
[No Author Listed] Dow Corning. Information About Low Viscosity Silicone Fluids: 200® Fluid, 5cs; 200® Fluid, 10cs; 200® Fluid, 20cs. Product Information Sheet. Form No. 25-941-97. 1997.(The year of publication is sufficiently earlier than the effective U.S. filing date and any foreign priority date so that the particular month of publication is not in issue. See MPEP 609.04(a)) 2 pages.
[No Author Listed] Dow Corning® 190 Fluid Product Data Sheet. Dow Corning 190 Fluid is a silicone glycol coploymer. Last accessed on Sep. 18, 2006 <https://www.dowcorning.com/applications/search/default.aspx?R=66EN> 1 page.
[No Author Listed] Dow Corning® 190 Fluid. INCI Name: PEG/PPG-18/18 Dimethicone. Production Information Sheet. Ref No. 22-1616C-01. Dated May 17, 2002. 4 pages.
[No Author Listed] Dow Corning® 190 Fluid. Material Safety Data Sheet. Version 1.6. Revision date Sep. 19, 2005. 7 pages.
[No Author Listed] Dow Corning® 190 Fluid. Textile, Leather & Non-woven. Silicone-ethylene oxide/propylene oxide copolymer. 3 pages.
[No Author Listed] Frequently Asked Questions: How long can I store liposomes? Avanti Polar Lipids, Inc. Last accessed on Jun. 13, 2007. <http://avantilipids.com/DisplayFAQ.asp?Q=3> 1 page.
[No Author Listed] Frequently Asked Questions: How should I store my liposomes? Avanti Polar Lipids, Inc. Last accessed on Jun. 13, 2007. <http://avantilipids.com/DisplayFAQ.asp?Q=1> 1 page.
[No Author Listed] Frequently Asked Questions: What are the differences between liposomes and micelles? Avanti Polar Lipids, Inc. Last accessed on Jun. 13, 2007. <http://avantilipids.com/DisplayFAQ.asp?Q=4> 1 page.
[No Author Listed] Frequently Asked Questions: What is an SUV and LUV and how do they differ? Avanti Polar Lipids, Inc. Last accessed on Jun. 13, 2007. <http://avantilipids.com/DisplayFAQ.asp?Q=22> 1 page.
[No Author Listed] Google Search Results for "polyenylphosphatidylcholine phosphatidylcholi". Searched Sep. 29, 2007. 2 pages.
[No Author Listed] Liposome. Wikipedia. Last accessed on Jun. 11, 2007. <http://en.wikipedia.org/wiki/Liposome> 3 pages.
[No Author Listed] Liquid Crystal. Wikipedia. Last accessed on Jun. 22, 2009. <http://en.wikipedia.org/wiki/Liquid_crystal> 13 pages.
[No Author Listed] Oxytocin. Wikipedia. Last accessed on May 4, 2011. <http://en.wikipedia.org/wiki/Oxytocin> 16 pages.
[No Author Listed] Phosal® 50 PG data sheet. Sep. 10, 2007; 1 page.
[No Author Listed] Phosphatidylcholine. (Monograph). Alternative Medicine Review. Apr. 1, 2002. last accessed online via http://www.encyclopedia.com/doc/1G1-85522987.html on Sep. 29, 2007. 9 pages.
[No Author Listed] Phospholipon® 80. Technical Data. American Lecithin Company. Date not known.
[No Author Listed] Preparations of liposomes. Avanti Polar Lipids, Inc. Last accessed on Jun. 13, 2007. <http://www.avantilipids.com/PreparationOfLiposomes.html> 3 pages.
[No Author Listed] Vasopressin. Wikipedia. Last accessed on May 4, 2011. <http://en.wikipedia.org/wiki/Vasopressin> 11 pages.
[No Author Listed], Poloxamer 407. Wikipedia Definition. Last Accessed on Feb. 1, 2013 from http://en.wikipedia.org/wiki/Poloxamer_407.

Abramson, Nitric oxide in inflammation and pain associated with osteoarthritis. Arthritis Res Ther. 2008;10 Suppl 2:S2. Epub Oct. 17, 2008. Review.
Ahn et al., Phase properties of liquid-crystalline Phosphatidylcholine/Phosphatidylethanolamine bilayers revealed by fluorescent probes. Arch Biochem Biophys. Sep. 15, 1999;369(2):288-94.
Bergenstahl et al., Phase equilibria in the system soybean lecithin/water. Progress in Colloid & Polymer Science. 1983;68:48-52. (The year of publication is sufficiently earlier than the effective U.S. filing date and any foreign priority date so that the particular month of publication is not in issue. See MPEP 609.04(a)).
Board Decision filed May 26, 2011 in co-pending U.S. Appl. No. 11/506,137.
Brandl et al., Morphology of semisolid aqueous phosphatidylcholine dispersions, a freeze fracture electron microscopy study. Chemistry and Physics of Lipids. May 30, 1997;87(1):65-72.
Cevc et al. "Ultraflexible Vesicles, Transfersomes, Have an Extremely Low Pore Penetration Resistance and Transport Therapeutic Amounts of Insulin Across the Intact Mammalian Skin." Biochem. et Biophys. Acta 1998, 1368, 201-215.
Cole et al., Challenges and opportunities in the encapsulation of liquid and semi-solid formulations into capsules for oral administration. Adv Drug Deliv Rev. Mar. 17, 2008;60(6):747-56. Epub Nov. 9, 2007.
Corswant et al., Triglyceride-based microemulsion for intravenous administration of sparingly soluble substances. J Pharm Sci. Feb. 1998;87(2):200-8.
Dermis [online] retrieved Jun. 21, 2013 from: en.wikipedia.org/wiki/Dermis. Wikipedia. 3 pages.
Engels et al., Liquid crystalline surfactant phases in chemical applications. J Mater Chem. 1998;8(6):1313-20. (The year of publication is sufficiently earlier than the effective U.S. filing date and any foreign priority date so that the particular month of publication is not in issue. See MPEP 609.04(a)).
Esposito, Elisabette et al., "Lipid-Based Supramolecular Systems for Topical Application: A Preformulatory Study," Published(Italy) Nov. 18, 2003, 15 pages. AAPS PharmSci 2003; 5(4) Article 30 (http://aapspharmsci.org).
Gad, Pharmaceutical Manufacturing Handbook: Production and Processes. John Wiley & Sons, Inc. New Jersey. 2008:1344.
Guo et al, "Transdermal Delivery of Insulin in Mice by Using Lecithin Vesicles as a Carrier," Drug Delivery, 7:113-116 (2000).
Huang et al., Nitric oxide-loaded echogenic liposomes for nitric oxide delivery and inhibition of intimal hyperplasia. J Am Coll Cardiol. Aug. 11, 2009;54(7):652-9.
Human Mouth [online] retrieved Jun. 21, 2013 from: en.wikipedia.org/wiki/Human_mouth. Wikipedia. 4 pages.
Imbert et al., Measuring the encapsulation of cosmetic ingredients into liposomes: a method for large, hydrophilic compounds. J Soc Cosmet Chem. Nov./Dec. 1996;47(6):337-49.
Kirsten et al., Polyenylphosphatidylcholine improves the lipoprotein profile in diabetic patients. International Journal of Clinical Pharmacology and Therapeutics. 1994;32(2):53-6. (The year of publication is sufficiently earlier than the effective U.S. filing date and any foreign priority date so that the particular month of publication is not in issue. See MPEP 609.04(a)).
Lawrence et al., Microemulsion-based media as novel drug delivery systems. Adv Drug Deliv Rev. Dec. 6, 2000;45(1):89-121.
Lecithin the Multipurpose Emulsicier for Foods; [online] retrieved on Apr. 5, 2013 from: http://bluecoat-02/?cfru=aHR0cDovL3d3dy5sZWNpdGluYS5pdC9wZGYvTGVjaXRoaW4IMjBUaGUIMjBNdwx0aXB1cnBvc2UIMjBlbXVsc21maWVyLnBkZg==; 8 pages.
Maeda et al., Preparation of poly(L-lactic acid)-polysiloxane-calcium carbonate hybrid membranes for guided bone regeneration. Biomaterials. Mar. 2006;27(8):1216-22. Epub Sep. 6, 2005.
Maurer et al., Developments in liposomal drug delivery systems. Expert Opin Biol Ther. 2001;1(6):1-25.
Miller et al., Recent developments in nitric oxide donor drugs. Br J Pharmacol. Jun. 2007;151(3):305-21. Epub Apr. 2, 2007.

(56) References Cited

OTHER PUBLICATIONS

Moller et al., Direct measurement of nitric oxide and oxygen partitioning into liposomes and low density lipoprotein. J Biol Chem. Mar. 11, 2005;280(10):8850-4. Epub Jan. 4, 2005.
Mueller-Goymann, Liquid crystals in drug delivery. Encylcopedia of Pharmaceutical Technology. 1988-2000;20:117-46. (The year of publication is sufficiently earlier than the effective U.S. filing date and any foreign priority date so that the particular month of publication is not in issue. See MPEP 609.04(a)).
O'Donnell et al., Nitration of unsaturated fatty acids by nitric oxide-derived reactive species. Methods Enzymol. 1999;301:454-70.
Prescott, Methods in Cell Biology. Academic Press. 1976. Chapter 4. p. 34, 4 pages.
Qi et al., Interactions of insulin with dipalmitoylphosphatidylcholine liposomes. Acta Pharma Sinica. Dec. 2000;35(12):924-8. Chinese.
Rawat et al., Lipid carriers: a versatile delivery vehicle for proteins and peptides. Yakugaku Zasshi. Feb. 2008;128(2):269-80.
Seabra et al., Topically applied S-nitrosothiol-containing hydrogels as experimental and pharmacological nitric oxide donors in human skin. Br J Dermatol. Nov. 2004;151(5):977-83.
Shah et al., Cubic phase gels as drug delivery systems. Adv Drug Deliv Rev. Apr. 25, 2001;47(2-3):229-50.
Subczynski et al., Permeability of nitric oxide through lipid bilayer membranes. Free Radic Res. May 1996;24(5):343-9.
Troxerutin. Last accessed Jun. 12, 2008. <http://chamicalland21.com/lifescience/uh/TROXERUTIN.htm> 2 pages.
Tyle, Liquid crystals and their applications in drug delivery. Controlled Release of Drugs: Polymers and Aggregate Systems. Chapter 4. Morton Rosoff Ed., VCH Publishers New York, NY. 1989, pp. 125-162.
Valenta et al., Evaluation of novel soya-lecithin formulations for dermal use containing ketoprofen as a model drug. J Control Release. Jan. 3, 2000;63(1-2):165-73.
Van Beek et al., Thyroid hormones directly alter human hair follicle functions: anagen prolongation and stimulation of both hair matrix keratinocyte proliferation and hair pigmentation. J Clin Endocrinol Metab. Nov. 2008;93(11):4381-8. Epub Aug. 26, 2008.
Wimalawansa, Nitric oxide: novel therapy for osteoporosis. Expert Opin Pharmacother. Dec. 2008;9(17):3025-44. Review. Erratum in: Expert Opin Pharmacother. Apr. 1, 2010;11(6):1043.
Yuen et al., Treatment of chronic painful diabetic neuropathy with isosorbide dinitrate spray: a double-blind placebo-controlled crossover study. Diabetes Care. Oct. 2002;25(10):1699-703.
International Report on Patentability for Application No. PCT/US2012/000151 mailed Sep. 26, 2013.
Office Action mailed Aug. 26, 2013 for U.S. Appl. No. 11/506,137.
Office Action mailed Aug. 26, 2013 for U.S. Appl. No. 13/019,101.
[No Author Listed] Phosal 50 PG MSDA 2007. 3 pages.
Agarwal et al., Preparation and In Vitro Evaluation of Miconazole Nitrate-Loaded Topical Liposomes. Pharmaceutical Technology. Nov. 2002, p. 48-60.
Barenholz et al., Handbook of nonmedical applications of liposomes. 1996;3:217.
Benson et al, "Optimization of Drug Delivery 4. Transdermal Drug Delivery," Aus J Hosp Pharm, 27(6): 441-448 (1997).
Bhattacharjee, "More Than the Patch: New Ways to Take Medicine Via Skin," New York Times, Jul. 2, 2002, p. F5.
Brannon-Peppas, "Polymers in Controlled Drug Delivery," Medical Plastics and Biomaterials Magazine, Nov. 1997.
CEVC, Transdermal Drug Carriers: Basic Properties, Optimization and Transfer Efficiency in the Case of Epicutaneously Applied Peptides, Journal of Controlled Release 36: 3-16 (1995).
Chapman, Phase transitions and fluidity characteristics of lipids and cell membranes. Q Rev Biophys. May 1975;8(2):185-235.
Chetty et al., Novel Methods of Insulin Delivery: An Update, Critical Reviews in Therapeutic Drug Carrier Systems, 15(6): 629-670 (1998).
Christie, Phosphatidylcholine and Related Lipids, www.lipid.co.uk, May 5, 2003.

Cox, Roundup's inert surfactant is poisonous. Journal of Pesticide Reform. 1988 Spring;8(1):30.
Daddona, Recent Advances in Peptide, Protein and Macromolecule Drug Delivery, Current Opinion in Drug Discovery & Development, 2(2): 168-171 (1999).
Daniels, "Galenic Principles of Modern Skin Care Products," Skin Care Forum, Issue 25, Apr. 2001.
King et al., Transdermal delivery of insulin from a novel biphasic lipid system in diabetic rats. Diabetes Technol Ther. 2002;4(4):479-88.
Maurer et al., Developments in liposomal drug delivery systems. Expert Opin Biol Ther. Nov. 2001;1(6):923-47.
Mitragotri, "Synergistic Effect of Enhancers for Transdermal Drug Delivery," Pharmaceutical Research, 17(11):1354-1359 (2000).
Patki et al., "Progress Made in Non-Invasive Insulin Delivery," Indian Journal of Pharmacology, 28:143-151 (1996).
Robin, A physiological handbook for teachers of yogasana. 2002:283-5.
Trehan et al., "Recent Approaches in Insulin Delivery," Drug Development and Industrial Pharmacy, 24(7): 589-97 (1998).
Weiner et al. "Liposome-Collagen Gel Matrix: A Novel Sustained Drug Delivery System." J. Pharm. Sci. 1985, 74(9), 922-5.
Office Action mailed Mar. 13, 2015 for U.S. Appl. No. 13/801,446.
Office Action mailed Jan. 14, 2015 for U.S. Appl. No. 13/801,518.
Office Action mailed Mar. 31, 2015 for U.S. Appl. No. 13/801,543.
Office Action mailed Jan. 7, 2015 for U.S. Appl. No. 13/800,952.
Office Action mailed Jan. 9, 2015 for U.S. Appl. No. 13/801,013.
Office Action mailed Feb. 27, 2015 for U.S. Appl. No. 13/801,061.
Office Action mailed Mar. 12, 2015 for U.S. Appl. No. 13/801,110.
Office Action mailed Jan. 5, 2015 for U.S. Appl. No. 13/801,188.
Office Action mailed Mar. 2, 2015 for U.S. Appl. No. 13/801,240.
Office Action mailed Feb. 27, 2015 for U.S. Appl. No. 13/801,345.
International Search Report and Written Opinion mailed Oct. 6, 2014 for PCT/US2014/025822.
International Search Report and Written Opinion mailed Oct. 6, 2014 for PCT/US2014/025913.
International Search Report and Written Opinion mailed Sep. 25, 2014 for PCT/U52014/025572.
International Search Report and Written Opinion mailed Oct. 6, 2014 for PCT/US2014/025630.
International Search Report and Written Opinion mailed Oct. 2, 2014 for PCT/US2014/025758.
International Search Report and Written Opinion mailed Oct. 6, 2014 for PCT/US2014/025898.
International Search Report and Written Opinion mailed Oct. 6, 2014 for PCT/US2014/025705.
Chu et al., The treatment of subclinical hypothyroidism is seldom necessary. The Journal of Clinical and Endocrinology and Metabolism. 2001; 86(10):4591-4599.
Gary et al., The thyrotropin-releasing hormone (TRH) hypothesis of homeostatic regulation: implications for TRH-based therapeutics. The Journal of Pharmacology and Experimental Therapeutics. 2003; 305(2):410-416.
Gaspar et al., Thyrotropin releasing hormone: selectively stimulats human hair follicle. Journal of Investigative Dermatology. 2011; 131.
Osborne et al., Modulation of peptide binding to specific receptors on rat pituitary cells by tumor-promoting phorbol esters: decreased binding of thyrotopin-releasing hormone and somatostatin as well as epidermal growth factor. Cancer Research. Nov. 1982; 42:4375-4381.
Schioth et al., Thyrotropin releasing hormone (TRH) selectively binds and activates the melanocortin 1 receptor. Peptides. 1990; 20:395-400.
Shekhter et al., Beneficial effect of gaseous nitric oxide on the healing of skin wounds. Nitric Oxide. Jun. 2005;12(4):210-9.
Xie et al., Therapy of cancer metastasis by activation of the inducible nitric oxide synthase. Cancer Metastasis Rev. Mar. 1998;17(1):55-75.
Office Action mailed Jun. 16, 2015 for U.S. Appl. No. 13/801,402.
Office Action mailed Jul. 16, 2015 for U.S. Appl. No. 13/801,446.
Office Action mailed Jul. 16, 2015 for U.S. Appl. No. 13/801,488.
Advisory Action mailed Apr. 23, 2015 for U.S. Appl. No. 13/801,518.
Advisory Action mailed Jul. 2, 2015 for U.S. Appl. No. 13/801,518.

(56) References Cited

OTHER PUBLICATIONS

Office Action mailed Jul. 20, 2015 for U.S. Appl. No. 13/800,952.
Office Action mailed Jul. 29, 2015 for U.S. Appl. No. 13/801,013.
Office Action mailed Jul. 29, 2015 for U.S. Appl. No. 13/801,061.
Office Action mailed Jul. 29, 2015 for U.S. Appl. No. 13/801,110.
Office Action mailed Jul. 29, 2015 for U.S. Appl. No. 13/801,188.
Office Action mailed Jun. 29, 2015 for U.S. Appl. No. 13/801,298.
Office Action mailed Jul. 30, 2015 for U.S. Appl. No. 13/801,345.
Office Action mailed May 7, 2015 for U.S. Appl. No. 14/096,098.
Office Action mailed Aug. 14, 2015 for U.S. Appl. No. 14/096,054.
Office Action mailed Sep. 1, 2015 for U.S. Appl. No. 14/096,056.
Office Action mailed Sep. 9, 2015 for U.S. Appl. No. 14/096,088.
Stewart et al., Gonadotropin and steroid hormones stimulate proliferation of the rat ovarian surface epithelium. J Cell Physiol. Jan. 2004;198(1):119-24.

* cited by examiner

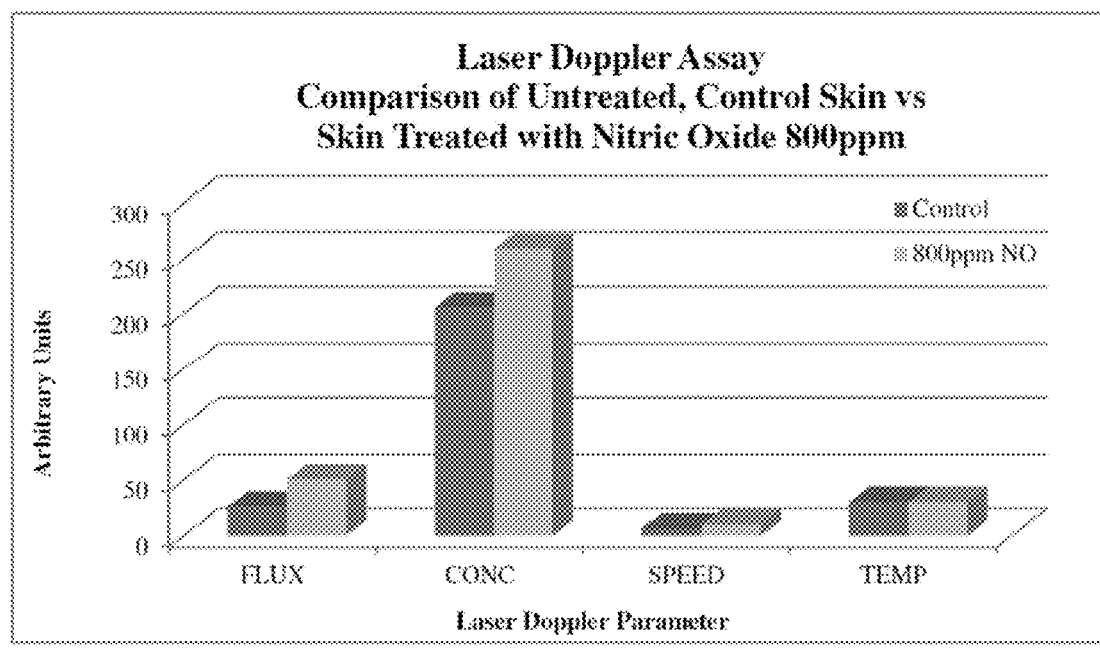

HAIR TREATMENT SYSTEMS AND METHODS USING PEPTIDES AND OTHER COMPOSITIONS

FIELD OF INVENTION

The present invention generally relates to compositions and methods for topical or transdermal delivery, and treatment of hair related conditions.

BACKGROUND

Topical drug delivery systems are known. These systems deliver drugs or other therapeutic agents, or other desired substances topically or transdermally, and may be designed to act locally at the point of application, or to act systemically once entering the body's blood circulation. In these systems, delivery may be achieved by techniques such as direct topical application of a substance or drug in the form of an ointment or the like, or by adhesion of a patch with a reservoir or the like that holds the drug (or other substance) and releases it to the skin in a time-controlled fashion.

Topical delivery systems for substances such as peptides, drugs, pain relieving compounds, vitamins, and skin or hair improving compounds have been in use for a number of years. Transdermal delivery systems using creams have been developed for use with analgesics and skin refining compounds. However, these delivery systems do not work effectively for all compounds. Further, effective topical delivery systems for providing therapeutic agents to treat hair related conditions such as hair loss and loss of hair pigmentation are needed.

SUMMARY

The present invention generally relates to compositions and methods for transdermal delivery, including treatment of hair or scalp conditions, such as baldness, thinning hair, and greying or loss of hair pigmentation. The subject matter of the present invention involves, in some cases, interrelated products, alternative solutions to a particular problem, and/or a plurality of different uses of one or more systems and/or articles.

In one aspect, the present invention is generally directed to a method comprising an act of administering, to the skin and/or hair of a subject, a composition comprising an effective amount of thyrotropin-releasing hormone (TRH) and nitric oxide to increase hair growth, and a carrier having a phosphatidylcholine component entrapping the nitric oxide.

In accordance with another aspect, the present invention is generally directed to a method comprising contacting the skin and/or hair of a subject with a composition comprising an emulsion comprising a first phase comprising TRH, nitric oxide, and lecithin, and a second phase comprising an emulsifier. The lecithin, in one set of embodiments, is present at least about 0.25% by weight of the composition. In some cases, the first phase comprises no more than about 250 ppm of water by weight of the composition.

In another aspect, the present invention encompasses methods of making one or more of the embodiments described herein, for example, a composition comprising nitric oxide. In still another aspect, the present invention encompasses methods of using one or more of the embodiments described herein, for example, a composition comprising nitric oxide.

Other advantages and novel features of the present invention will become apparent from the following detailed description of various non-limiting embodiments of the invention. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWING

FIG. 1 shows results from the laser Doppler assay in four human study participants.

DETAILED DESCRIPTION

The present invention generally relates to compositions and methods for transdermal delivery, and treatment of hair related conditions. The compositions can be used in a variety of applications, including causing or promoting hair growth and/or hair pigmentation. In some cases, the composition may include nitric oxide and/or peptides. The nitric oxide and/or peptide may be present within a first phase comprising a lecithin, such as phosphatidylcholine. In certain embodiments, the lecithin is present in liposomes, micelles, or other vesicles containing nitric oxide, peptides, or both. The composition can take the form of a gel, a cream, a lotion, an ointment, a solution, a solid "stick," etc., that can be rubbed or sprayed onto the skin, e.g., onto the scalp, or other suitable portion of the skin. Other aspects of the present invention are generally directed to methods of making or using such compositions, methods of promoting such compositions, kits including such compositions, or the like.

According to one aspect of the present invention, a composition as described herein is used to treat various hair related conditions such as those described herein. Thus, in one set of embodiments, the application of nitric oxide and/or peptide, e.g., in a nitric oxide and/or peptide matrix, to the skin or hair of a subject may result in improvement. In some cases, the delivery of nitric oxide and/or peptides to the skin, e.g., to the epidermis and/or dermis, may be achieved at a controlled rate and/or concentration. Without wishing to be bound by any theory, it is believed that nitric oxide may increase vasodilation, and/or promote beneficial neural signaling.

In still another aspect, peptides are provided which are useful as therapeutic agents, e.g. in the treatment of baldness, thinning hair, loss of hair pigmentation (e.g. greying of the hair), etc. In some aspects, compositions comprising peptides provided herein are effective in treating baldness, thinning hair, loss of hair pigmentation (e.g. greying of the hair) etc., alone or in combination, e.g. in a common composition with, nitric oxide. In some cases, the peptide may include two or more amino acids linked by the carboxyl group of one amino acid to the amino group of another, e.g. a peptide linkage, to form an amino acid sequence. It is contemplated that peptides may be purified and/or isolated from natural sources or prepared by recombinant or synthetic methods. Amino acid sequences may be encoded by naturally or non-naturally occurring nucleic acid sequences or synthesized by recombinant nucleic acid sequences or artificially synthesized. A peptide may be a linear peptide or a cyclopeptide, e.g. cyclic including bicyclic. In some cases, a "peptide" may be interchangeably referred to as a "therapeutic peptide." In some cases, the peptide is a "pseudo-peptide" or a "peptidomimetic," which are compounds designed to functionally mimic a peptide. Non-limiting examples of peptides include thyrotropin-releasing hormone (TRH) or melanocyte-stimulating hormone (MSH).

In certain preferred embodiments, the peptide is thyrotropin-releasing hormone (TRH), or an analog thereof. Non-limiting examples of TRH or TRH analogs contemplated by the present invention include protirelin (Thyrel TRH, Relafect TRH), taltirelin (Ceredist), montirelin, as well as salts and analogs of any of the foregoing. Without wishing to be bound by any theory, TRH is believed to promote hair-shaft elongation, prolong the hair cycle growth phase (anagen), and/or increase proliferation of (while inhibiting apoptosis of) hair matrix keratinocytes. Further (without wishing to be bound by any theory), TRH may stimulate melanin synthesis, tyrosinase transcription and activity, melanosome formation, and melanocyte dendricity in human hair follicles. Thus, compositions comprising nitric oxide and/or TRH may be used in certain embodiments for the treatment or prevention of hair loss and/or loss of hair pigmentation.

In addition, again without wishing to be bound by any theory, TRH may also increase or upregulate paraoxonase activity (e.g., paraoxonase 1) in some cases. For example, TRH may increase paraoxonase production, which can result in increased blood flow, which can be used to stimulate hair follicle growth. In addition, TRH may act synergistically with NO, since NO may also causes an increase in blood flow, among other effects as described herein. Accordingly, applying TRH and nitric oxide to a subject may be used to stimulate hair growth, at least in certain embodiments.

In still another embodiment, nitric oxide and/or peptide containing compositions described herein further comprise one or more therapeutic agents effective in treating hair loss, e.g. by promoting hair growth and/or preventing further hair loss. Non-limiting examples of such agents include minoxidil, finasteride, dutasteride, dithranol (anthralin), and/or corticosteroids.

In some cases, the compositions and methods described herein are used to stimulate the absorption of nitric oxide and/or peptides into cells and tissues, and/or promote vasodilation of skin tissues, e.g., near hair. Certain aspects of the present invention thus permit treatment or prevention of various symptoms such as hair loss, thinning hair, loss of hair pigmentation, greying of the hair, etc.

In some embodiments, certain compositions of the present invention may be applied to a subject to promote hair growth, for example in a region where hair growth is desired. In some embodiments, for example, a composition can be applied to the skin of a subject, for example, to prevent or reduce hair loss, for example in a region where hair loss is undesirable. In some embodiments, a region targeted for hair growth and or a reduction in hair loss may be the skin surface of the scalp. In some embodiments, a subject may be a human. The subject may be male or female.

In some embodiments, a subject may have lost hair (e.g., is bald, balding, or has thinning hair) and/or may be at risk of losing hair (e.g., due to age, a genetic risk and/or family history of hair loss). In some embodiments, the subject may have lost hair or be at risk for losing hair due to injury (e.g., trauma or burn) or due to a disease and/or treatment (e.g., chemotherapy). In some embodiments, the subject has genetic pattern hair loss (e.g. androgenetic alopecia) or non-scarring alopecia (e.g. alopecia areata).

In still another embodiment, certain compositions of the present invention may be applied to a subject to promote hair pigmentation, for example in a region where hair pigmentation is desired. In some embodiments, a composition can be applied to the skin of a subject, for example, to prevent or reduce loss of hair pigmentation (e.g. greying of the hair), for example in a region where loss of hair pigmentation is undesirable. In some embodiments, a region targeted for promoting hair pigmentation and/or a reduction in loss of hair pigmentation may be the skin surface of the scalp. In some embodiments, a subject may be a human. The subject may be male or female. In some embodiments, a subject may have lost hair pigmentation (e.g., has grey or greying hair) and/or may be at risk of losing hair pigmentation (e.g., due to age, a genetic risk and/or family history of greying hair). In some embodiments, the subject may have lost hair pigmentation or be at risk for losing hair pigmentation due to injury (e.g., trauma or burn) or due to a disease and/or treatment (e.g., chemotherapy).

Without wishing to be bound by any theory, it is believed that increased blood flow in certain desired areas of a subject, e.g. the scalp, is beneficial in the treatment of hair loss and/or loss of hair pigmentation, as nutrients in the blood are made more available to the hair follicle, while certain negative factors, e.g. dihydrotestosterone (DHT), are more rapidly cleared from the hair follicle. For example, nitric oxide may be introduced to subjects to stimulate or support vasodilatation, anti-inflammation, anti-bacteria, and in particular modulation of the hair cycle.

Thus, in one set of embodiments, application of nitric oxide and/or peptides, e.g., in a penetrating matrix gel delivering the active nitric oxide and/or peptide, may be applied to the skin of a subject, e.g., as described herein. Additionally, in some embodiments, the composition may be applied in conjunction with other types of treatments to a subject, e.g., to the skin of a subject, e.g., as described herein. These may be occur, e.g., simultaneously or sequentially, in various embodiments.

In certain embodiments of the present invention, nitric oxide gas itself is entrapped or contained within various compositions as discussed herein, for example, in liquid crystal multilamellar phosphatidylcholine. In addition, in certain embodiments as discussed below, the composition may be stable and can be stored for periods of time with little or no loss or reaction of the nitric oxide contained therein.

In some embodiments, the nitric oxide and/or the peptide within the composition is stable at room temperature, and may remain active for extended periods of time, for example, for at least 1 year, at least 2 years, at least 3 years, at least 4 years, etc. The nitric oxide and the peptide may be released, for example, when the composition is exposed to an aqueous environment, e.g., within the body. Without wishing to be bound by any theory, it is believed that when the composition is applied to the skin, the liquid crystal structure collapses, delivering nitric oxide and/or the peptides to, e.g., a muscle or other desired area of treatment. The concentration of the nitric oxide and the peptide inside the liquid crystal matrix can be varied in terms of concentration. The matrix also may act as a sustained release and delivery system in some embodiments. It is also believed that the liquid crystal is highly penetrating, such that nitric oxide and the peptide can be delivered to the epidermis, dermis and dermal vascular for systemic release as well as to subcutaneous fat, at least under some conditions.

Since nitric oxide is an unstable and reactive gas, entrapment, storage, and release of nitric oxide requires careful formulation in some embodiments of the invention. For example, nitric oxide readily reacts with water to form nitrous acid ($HNO_2$), and thus, certain embodiments of the invention include compositions or phases that are substantially free of water. As another example, in one set of embodiments, nitric oxide and/or peptides may be contained within a first phase comprising a lecithin such as phosphatidylcholine, which may be present within a second phase comprising an emulsifier, such as is discussed herein. Other components, for example, transdermal penetration enhancers, adjuvants, surfactants, lubricants, etc. can also be present in certain cases.

Thus, the compositions of the invention comprise, in certain aspects, a phase comprising phosphatidylcholine and/or other lecithins in which nitric oxide and/or peptide is contained within or "trapped." The phosphatidylcholine or lecithin may be contained within a second phase, for example, comprising an emulsifier, which may cause the phosphatidylcholine or lecithin to form vesicles, e.g., micelles or liposomes. The phosphatidylcholine or lecithin composition can be unilamellar or multilamellar in some embodiments. In some instances, the presence of the second phase causes the phosphatidylcholine or lecithin to form a liquid crystal arrangement.

The nitric oxide is typically gaseous, and may be present within the composition as small bubbles and/or bound to lecithins or phosphatidylcholines within the composition. For example, the nitric oxide may be bound to double bonds present in the lecithins or phosphatidylcholines. Phosphatidylcholine is believed to stabilize and/or contain the nitric oxide and/or peptide. In some cases, stability of the composition can be achieved at room temperature (about 25° C.), and/or at other temperatures such as those described herein. Without wishing to be bound by any theory, it is believed that the phosphatidylcholine adopts a liquid crystal structure under such conditions, which can thereby contain the nitric oxide, e.g., as small gaseous bubbles, and/or through binding with lecithins or phosphatidylcholines. Similarly (without wishing to be bound by any theory), it is contemplated that peptides are also contained within the vesicular and/or liquid crystal structure of phosphatidylcholine or other carriers described herein. In some aspects, (without wishing to be bound by any theory) the peptide, depending on its hydrophobicity, may be contained within phosphatidylcholine vesicular membrane, or may be tightly associated with the inner or outer surface of the membrane.

Nitric oxide is typically reactive with water (e.g., forming nitrous acid), which contributes to its relatively short lifetime within the body or within other aqueous environments. Accordingly, in certain embodiments of the invention, the composition, or at least a phase of the composition comprising the nitric oxide (and/or the second phase, and/or one or more materials used to prepare a nitric oxide composition, and/or a nitric oxide composition prepared as described herein), is substantially free of water, e.g., comprising no more than about 10 wt %, no more than about 3 wt %, no more than about 1 wt %, no more than about 0.3 wt %, or no more than about 0.1 wt % water (i.e., relative to the weight of the overall composition). The composition may also have no more than about 1,000 ppm, no more than about 750 ppm, no more than about 500 ppm, no more than about 400 ppm, no more than about 300 ppm, no more than about 250 ppm, no more than about 200 ppm, no more than about 150 ppm, no more than about 100 ppm, no more than about 50 ppm, no more than about 25 ppm, or no more than about 10 ppm of water. In certain embodiments, no detectable water may be present in the composition, or at least within a phase of the composition comprising the nitric oxide. Any suitable technique can be used for determining the amount of water present in the composition, for example, Karl-Fisher titration. In some cases, the composition may also be free of any liquids that typically contain water, e.g., physiological buffers, body fluids, saline, or the like.

Any suitable amount of nitric oxide may be present within a composition prepared as described herein. For example, at least about 0.3 wt %, at least about 0.5 wt %, at least about 0.7 wt %, at least about 1 wt %, at least about 1.5 wt %, at least about 2 wt %, at least about 2.5 wt %, at least about 3 wt %, at least about 5 wt % at least about 10 wt %, at least about 20 wt %, at least about 30 wt %, at least about 40 wt %, at least about 50 wt %, at least about 60 wt %, at least about 70 wt %, at least about 80 wt %, at least about 90 wt %, at least about 100 wt %, at least about 110 wt %, or at least about 120 wt % of the composition can be nitric oxide, where the basis of the weight percentage is the weight of the composition before nitric oxide is added. For example, the nitric oxide may be present at between 70 wt % and about 120 wt % of the composition.

In some embodiments, the nitric oxide may be present at a concentration of at least about 400 mg/kg, at least about 450 mg/kg, at least about 500 mg/kg, at least about 550 mg/kg, at least about 570 mg/kg, at least about 600 mg/kg, at least about 650 mg/kg, at least about 700 mg/kg, at least about 750 mg/kg, at least about 800 mg/kg, at least about 850 mg/kg, at least about 950 mg/kg, or at least about 1000 mg/kg of the composition. In certain cases, the nitric oxide may be present at a concentration of no more than about 2000 mg/kg, no more than about 1500 mg/kg, no more than about 1000 mg/kg, no more than about 960 mg/kg, no more than about 900 mg/kg, no more than about 800 mg/kg, no more than about 700 mg/kg, or no more than about 600 mg/kg. For example, the nitric oxide may be present at a concentration of between about 570 mg/kg and about 960 mg/kg.

In some embodiments, the nitric oxide is present at a concentration (e.g., on a per-mass basis) of at least about 100 ppm, at least about 200 ppm, at least about 300 ppm, at least about 400 ppm, at least about 500 ppm, at least about 600 ppm, at least about 700 ppm, at least about 800 ppm, at least about 900 ppm, at least about 1000 ppm, at least about 1100 ppm, at least about 1200 ppm, at least about 1300 ppm, at least about 1400 ppm, at least about 1500 ppm, at least about 1600 ppm, at least about 1700 ppm, at least about 1800 ppm, at least about 1900 ppm, at least about 2000 ppm, at least about 2500 ppm, at least about 3000 ppm, at least about 3500 ppm, at least about 4000 ppm, at least about 4500 ppm, at least about 5000 ppm, at least about 6000 ppm, at least about 7000 ppm, at least about 8000 ppm, at least about 9000 ppm, or at least about 10000 ppm of the composition. In other embodiments, the nitric oxide is present at a concentration of no more than about 11000 ppm, no more than about 10000 ppm, no more than about 9000 ppm, no more than about 8000 ppm, no more than about 7000 ppm, no more than about 6000 ppm, no more than about 5000 ppm, no more than about 4500 ppm, no more than about 4000 ppm, no more than about 3500 ppm, no more than about 3000 ppm, no more than about 2500 ppm, no more than about 2000 ppm, no more than about 1900 ppm, no more than about 1800 ppm, no more than about 1700 ppm, no more than about 1600 ppm, no more than about 1500 ppm, no more than about 1400 ppm, no more than about 1300 ppm, no more than about 1200 ppm, no more than about 1100 ppm, no more than about 1000 ppm, no more than about 900 ppm, no more than about 800 ppm, no more than about 700 ppm, no more than about 600 ppm, no more than about 500 ppm, no more than about 400 ppm, or no more than about 300 ppm of the composition. For example, in some embodiments, nitric oxide is present at a concentration of between about 400 and about 900 ppm. NO content can be measured by any suitable technique. For example, in some embodiments, NO content is measured using a nitric oxide biosensor (e.g., nitric oxide macrosensor with nitric oxide specific electrode from WPI Instruments). In some embodiments, NO content is measured by a change in weight in the composition after adding NO.

In some embodiments, nitric oxide and/or peptide is present within a first phase comprising a lecithin, such as phosphatidylcholine. Phosphatidylcholine (herein abbreviated "PC") is a basic component of cell membrane bilayers and the main phospholipid circulating in the plasma of blood. Phosphatidylcholine typically has a phospholipid structure with a choline head group and a glycerophosphoric acid tail group. The tail group can be saturated or unsaturated. More than one tail group may be present in the phosphatidylcholine in some cases, and the tail groups may be the same or different. Specific non-limiting examples of phosphatidylcholines that could be used include one or a mixture of stearic, palmitic, margaric, and/or oleic acid diglycerides linked to a choline ester head group.

Phosphatidylcholines are a member of a class of compounds called lecithins. Typically, a lecithin is a composed of phosphoric acid, choline, fatty acids, glycerol, glycolipids, triglycerides, and/or phospholipids. In some cases, other lecithins may be used, in addition to or instead of a phosphatidylcholine. Non-limiting examples of other lecithins include phosphatidylethanolamine, phosphatidylinositol, or phosphatidic acid. Many commercial lecithin products are available, such as, for example, Lecithol®, Vitellin®, Kelecin®, and Granulestin®. Lecithin is widely used in the food industry. In some embodiments, certain compositions of the invention can contain synthetic or natural lecithin, or mixtures thereof. Natural preparations are used in some cases because they exhibit desirable physical characteristics, and/or may be economical or nontoxic. However, in other embodiments, non-natural preparations are used, or the composition can include both natural and non-natural preparations.

Any suitable amount of phosphatidylcholine or lecithin may be present within the composition. For example, at least about 0.25 wt %, at least about 0.5 wt %, at least about 1 wt %, at least about 2 wt %, at least about 3 wt %, at least about 5 wt %, at least about 8 wt %, at least about 10 wt %, at least about 20 wt %, at least about 30 wt %, at least about 40 wt %, at least about 50 wt %, at least about 60 wt %, at least about 70 wt %, at least about 80 wt %, or at least about 90 wt % of the entire composition can be a phosphatidylcholine or a lecithin. In some cases, the phosphatidylcholine or lecithin may be present at a concentration of no more than about 95 wt %, no more than about 90 wt %, no more than about 80 wt %, no more than about 70 wt %, no more than about 65 wt %, no more than about 60 wt %, no more than about 50 wt %, no more than about 40 wt %, no more than about 30 wt %, no more than about 20 wt %, or no more than about 10 wt %. For instance, the phosphatidylcholine or lecithin may be present at between about 8 wt % and about 65 wt %, or between about 0 wt % and about 10 wt %, etc. One or more than one type of phosphatidylcholine or lecithin may be present.

Some delivery compositions of the present invention may contain polyenylphosphatidylcholine (herein abbreviated "PPC"). In some cases, PPC can be used to enhance epidermal penetration. The term "polyenylphosphatidylcholine," as used herein, means any phosphatidylcholine bearing two fatty acid moieties, wherein at least one of the two fatty acids is an unsaturated fatty acid with at least two double bonds in its structure, such as linoleic acid.

Certain types of soybean lecithin and soybean fractions, for example, can contain higher levels of polyenylphosphatidylcholine, with dilinoleoylphosphatidylcholine (18:2-18:2 phosphatidylcholine) as the most abundant phosphatidylcholine species therein, than conventional food grade lecithin. Such lecithins may be useful in formulating certain delivery compositions. In some embodiments, conventional soybean lecithin may be enriched with polyenylphosphatidylcholine, for instance, by adding soybean extracts containing high levels of polyenylphosphatidylcholine. As used herein, this type of phosphatidylcholine is called "polyenylphosphatidylcholine-enriched" phosphatidylcholine (hereinafter referred to as PPC-enriched phosphatidylcholine), even where the term encompasses lecithin obtained from natural sources exhibiting polyenylphosphatidylcholine levels higher than ordinary soybean varieties. These products are commercially available, for example, from American Lecithin Company, Rhone-Poulenc and other lecithin vendors. American Lecithin Company markets its products with a "U" designation, indicating high levels of unsaturation; Rhone-Poulenc's product is a soybean extract containing about 42% dilinoleoylphosphatidylcholine and about 24% palmitoyllinoleylphosphatidylcholine (16:0 to 18:2 of PC) as the major phosphatidylcholine components. Another example of a suitable polyenylphosphatidylcholine is NAT 8729 (also commercially available from vendors such as Rhone-Poulenc and American Lecithin Company).

Any suitable amount of polyenylphosphatidylcholine may be present within the composition. For example, at least about 0.25 wt %, at least about 0.5 wt %, at least about 1 wt %, at least about 2 wt %, at least about 3 wt %, at least about 5 wt %, at least about 8 wt %, at least about 10 wt %, at least about 20 wt %, at least about 30 wt %, at least about 40 wt %, at least about 50 wt %, at least about 60 wt %, at least about 70 wt %, at least about 80 wt %, or at least about 90 wt % of the composition can be polyenylphosphatidylcholine. In some cases, the polyenylphosphatidylcholine may be present at a concentration of no more than about 95 wt %, no more than about 90 wt %, no more than about 80 wt %, no more than about 70 wt %, no more than about 65 wt %, no more than about 60 wt %, no more than about 50 wt %, no more than about 40 wt %, no more than about 30 wt %, no more than about 20 wt %, or no more than about 10%. For instance, the polyenylphosphatidylcholine may be present at between about 8 wt % and about 65 wt %. In some embodiments, at least about 20 wt %, at least about 30 wt %, at least about 40 wt %, at least about 50 wt %, at least about 60 wt %, at least about 70 wt %, at least about 80 wt %, at least about 90 wt %, or about 100 wt % of all of the phosphatidylcholine or lecithin in the composition is polyenylphosphatidylcholine.

While not wishing to be bound to any theory, it is believed that the PPC-enriched phosphatidylcholine forms a bilayer enveloping nitric oxide and/or peptides (and in some embodiments, other adjunct ingredients, if present) to create the composition. The PPC-enriched phosphatidylcholine is believed to contribute to the stability of the nitric oxide and/or peptide, for example, by shielding the nitric oxide and/or peptide from water, and/or by enhancing its penetration into the skin or other area, e.g., the scalp.

The first phase also comprises, in some embodiments of the invention, a fatty acid ester. Non-limiting examples include ascorbate palmitate or isopropyl palmitate. In some cases, the fatty acid ester is used as a preservative or an antioxidant. The composition can include any suitable amount of fatty acid ester, for example, at least about 1 wt %, at least about 3 wt %, at least about 5 wt %, at least about 10 wt %, at least about 20 wt %, at least about 30 wt %, at least about 40 wt %, at least about 50 wt %, etc. In some cases, no more than about 60 wt %, no more than about 50 wt %, no more than about 40 wt %, no more than about 30 wt %, no more than about 20 wt %, no more than about 18 wt %, no more than about 15 wt %, no more than about 12 wt %, or no more than about 10 wt % of the composition is fatty acid ester. For example, the composition may be between about 0 wt % and about 10 wt % fatty acid ester. The composition may include one or more than one fatty acid ester.

In certain embodiments, a composition such as those described herein can be formulated to include a second phase. Typically, the second phase is substantially immiscible with the first phase comprising phosphatidylcholine or lecithin. Two phases that are substantially immiscible are able to form discrete phases when exposed to each other at ambient conditions (e.g., 25° C. and 1 atm) for extended periods of time (e.g., at least about a day). The phases can be separate identifiable phases (e.g., one may float above the other), or in some cases, the phases are intermingled, e.g., as in an emulsion. The stability of the discrete phases may be kinetic and/or thermodynamic in nature, in various embodiments.

In one set of embodiments, the second phase may comprise an emulsifier which causes the first phase comprising phosphatidylcholine or lecithin to form a liquid crystal, and/or vesicles such as micelles or liposomes. Typically, in a liquid crystal phase, vesicular structures such as micelles, liposomes, hexagonal phases, or lipid bilayers can be formed. In some cases, multilamellar structures may be present within the liquid crystal phase, although in other cases, only unilamellar structures may be present. For example, in certain cases, the PPC-enriched phosphatidylcholine can be loosely arranged in a multilamellar fashion, with nitric oxide and/or peptides and optional adjunct ingredients being bonded or otherwise entrapped or contained within the lipid bilayers formed therein. In some cases, the first phase (e.g., comprising PPC-enriched phosphatidylcholine) and the second phase can form a structure such as is disclosed in U.S. Pat. No. 7,182,956 to Perricone, et al. This is believed (without wishing to be bound by any theory) to form a loosely arranged, yet stable, PPC-enriched phosphatidylcholine-drug complex that may allow penetration and delivery of nitric oxide and/or peptides and optional adjunct ingredients to the skin, e.g., to the dermal vasculature or to the scalp.

In one set of embodiments, the second phase comprises an emulsifier. The emulsifier, in one embodiment, is a substance that is able to stabilize an emulsion by increasing its kinetic stability. The emulsifier may also be chosen in some cases to be relatively inert or non-toxic relative to the skin, e.g. to the scalp.

In some embodiments, the second phase may comprise a polyglycol. The polyglycol may include a polyhydric alcohol of a monomeric glycol such as polyethylene glycol (PEG) and/or polypropylene glycol (PPG). For example, the PEG or PPG may be PEG or PPG 200, 300, 400, 600, 1,000, 1,450, 3,350, 4,000, 6,000, 8,000, and 20,000, where the number indicates the approximate average molecular weight of the PEG or PPG. As is understood by those of ordinary skill in the art, a polyglycol composition often will comprise a range of molecular weights, although the approximate average molecular weight is used to identify the type polyglycol. More than one PEG and/or PPG can also be present in certain instances.

The second phase may comprise a surfactant in some embodiments. Non-limiting examples of surfactants include a siloxylated polyether comprising dimethyl, methyl(propylpolyethylene oxide propylene oxide, acetate) siloxane commercially available from vendors such as Dow Corning (Dow Corning 190 surfactant). Other examples of materials that can be used as (or within) the second phase include, but are not limited to, 1,2-propanediol, or silicone fluids containing low viscosity polydimethylsiloxane polymers, methylparaben (p-hydroxy benzoic acid methyl ester) commercially available from vendors such as Dow Corning (Dow Corning 200 silicone fluid). Still other examples include various siloxane or silicone compounds, e.g., hexamethyldisiloxane, amodimethicone, phenyltrimethicone, etc.

Additionally, purified water may be added to the second phase in some embodiments, although in other cases, little or no water is present in the second phase. For example, the first phase, the second phase, can contain less than 10%, less than 5%, less than 2%, less than 1%, or less that 0.05% (e.g., wt %) of water relative to the weight of the respective phase or of the entire composition. In some cases, the second phase may also comprise adjunct ingredients such as those described herein.

The second phase may include any one, or more than one, of the materials described above. In addition, any suitable amount of second phase can be used in accordance with various embodiments of the invention. For example, the second phase may be present at at least about 10 wt %, at least about 20 wt %, at least about 30 wt %, at least about 40 wt %, at least about 50 wt %, at least about 60 wt %, at least about 70 wt %, at least about 80 wt %, or at least about 90 wt % of the composition. In some cases, the ratio of the first phase (e.g., comprising phosphatidylcholine or lecithin) to the second phase can be at least about 1:3, at least about 1:2, at least about 1:1, at least about 2:1, at least about 3:1, or at least about 4:1, etc.

In certain embodiments, a composition such as those described herein, e.g., those containing a peptide, and in some aspects also containing nitric oxide, may comprise a polyglycol. The polyglycol may include a polyhydric alcohol of a monomeric glycol such as polyethylene glycol (PEG) and/or polypropylene glycol (PPG). For example, the PEG or PPG may be PEG or PPG 200, 300, 400, 600, 1,000, 1,450, 3,350, 4,000, 6,000, 8,000, and 20,000, where the number indicates the approximate average molecular weight of the PEG or PPG. As is understood by those of ordinary skill in the art, a polyglycol composition often will comprise a range of molecular weights, although the approximate average molecular weight is used to identify the type polyglycol.

More than one PEG and/or PPG can also be present in certain instances. The composition can include any suitable amount of polyglycol, for example, at least about 1 wt %, at least about 3 wt %, at least about 5 wt %, at least about 10 wt %, at least about 20 wt %, at least about 30 wt %, at least about 40 wt %, at least about 50 wt %, etc. In some cases, no more than about 60 wt %, no more than about 50 wt %, no more than about 40 wt %, no more than about 30 wt %, no more than about 20 wt %, no more than about 18 wt %, no more than about 15 wt %, no more than about 12 wt %, or no more than about 10 wt % of the composition is polyglycol. For example, the composition may be between about 0 wt % and about 10 wt % polyglycol. The composition may include one or more than one type of polyglycol.

In some aspects, the formulation comprises a phosphatidylcholine, e.g., any of those described herein (Phospholipon-90G (American Lecithin Company)). The composition can include any suitable amount of phosphatidylcholine, for example, at least about 1 wt %, at least about 3 wt %, at least about 5 wt %, at least about 10 wt %, at least about 20 wt %, at least about 30 wt %, at least about 40 wt %, at least about 50 wt %, at least about 60 wt %, at least about 70 wt %, at least about 80 wt %, at least about 90 wt % etc. In some cases, no more than about 90 wt %, no more than about 80 wt %, no more than about 70 wt %, no more than about 60 wt %, no more than about 50 wt %, no more than about 40 wt %, no more than about 30 wt %, no more than about 20 wt %, no more than about 10 wt %, or no more than about 5 wt % of the composition is phosphatidylcholine. For example, the composition may be between about 0 wt % and about 10 wt % surfactant. The composition may include one or more than one phosphatidylcholine. Other examples of materials that can be used as (or within) the formulation include, but are not limited to, benzyl alcohol, ethyl alcohol, isopropyl palmitate (IPP), propanediol, and caprylic/capric triglycerides.

Any suitable amount of peptide may be present within a composition prepared as described herein. For example, the peptide may be present at a concentration, with respect to the volume of carrier (in cubic centimeters) containing the peptide, of at least about 0.01 mg/cc, at least about 0.02 mg/cc, at least about 0.03 mg/cc, at least about 0.04 mg/cc, at least about 0.05 mc/cc, at least about 0.06 mg/cc, at least about 0.07 mg/cc, at least about 0.08 mg/cc, at least about 0.09 mg/cc, at least about 0.10 mg/cc, at least about 0.20 mg/cc, at least about 0.30 mg/cc, at least about 0.40 mg/cc, at least about 0.50 mg/cc, at least about 0.60 mg/cc, at least about 0.70 mg/cc, at least about 0.80 mg/cc, at least about 0.90 mg/cc, at least about 1.0 mg/cc, at least about 1.5 mg/cc, at least about 2.0 mg/cc, at least about 2.5 mg/cc, at least about 3.0 mg/cc, at least about 3.5 mg/cc, at least about 4.0 mg/cc, at least about 4.5 mg/cc, at least about 5.0 mg/cc, at least about 5.5 mg/cc, at least about 6.0 mg/cc, at least about 6.5 mg/cc, at least about 7.0 mg/cc, at least about 7.5 mg/cc, at least about 8.0 mg/cc, at least about 8.5 mg/cc, at least about 9.0 mg/cc, at least about 9.5 mg/cc, at least about 10.0 mg/cc, at least about 15.0 mg/cc, at least about 20.0 mg/cc, at least about 25.0 mg/cc, at least about 30.0 mg/cc, at least about 35.0 mg/cc, at least about 40.0 mg/cc, at least about 45.0 mg/cc, at least about 50.0 mg/cc, at least about 60.0 mg/cc, at least about 70.0 mg/cc, at least about 80.0 mg/cc, at least about 90.0 mg/cc, at least about 100 mg/cc, at least about 125 mg/cc, at least about 150 mg/cc, at least about 175 mg/cc, at least about 200 mg/cc, at least about 250 mg/cc, at least about 300 mg/cc, at least about 400 mg/cc, at least about 500 mg/cc, at least about 750 mg/cc, or at least about 1000 mg/cc.

In certain cases, the peptide may be present at a concentration of no more than about 1500 mg/cc, no more than about 1000 mg/cc, no more than about 800 mg/cc, no more than about 600 mg/cc, no more than about 400 mg/cc, no more than about 200 mg/cc, no more than about 100 mg/cc, no more than about 75 mg/cc, no more than about 50 mg/cc, no more than about 25 mg/cc, no more than about 20 mg/cc, no more than about 15 mg/cc, no more than about 12.5 mg/cc, no more than about 10.0 mg/cc, no more than about 9.0 mg/cc, no more than about 8.0 mg/cc, no more than about 7.0 mg/cc, no more than about 6.0 mg/cc, no more than about 5.5 mg/cc, no more than about 5.0, no more than about 4.5 mg/cc, no more than about 4.0 mg/cc, no more than about 3.5 mg/cc, no more than about 3.0 mg/cc, no more than about 2.5 mg/cc, no more than about 2.0 mg/cc, no more than about 1.5 mg/cc, no more than about 1.0 mg/cc, no more than about 0.5 mg/cc, no more than about 0.1 mg/cc, or no more than about 0.01 mg/cc. For example, the peptide may be present at a concentration of between about 0.5 mg/cc and about 50.0 mg/cc. In some embodiments, the composition also comprises a suitable amount of nitric oxide, e.g., as provided herein.

In some embodiments, the peptide may be added to a composition during or after the formulation of any phase or composition as described herein, e.g., by routine methods known in the art. For example, the peptide may be added to any phase of a formulation or composition, or after any formulation or composition described herein is made. In some cases, for example, the peptide may be added before or after nitric oxide is added to the mixture, or before or after the first and second phases are mixed together. The peptide may be added to either the first phase or the second phase, depending on the type of peptide. In some cases, the peptide may be added after the first phase or the second phase after emulsification. The peptide may be present in a hydrophilic portion (e.g., a first portion) or a hydrophobic portion (e.g., a second portion) of a formulation, depending on the peptide. For example, if the formulation is an emulsion, a hydrophilic peptide may be contained within a hydrophilic phase of the emulsion, while a hydrophobic peptide may be contained within a hydrophobic phase of the emulsion; a peptide having both hydrophilic portions and hydrophobic portions may be contained at an interface between hydrophilic and hydrophobic phases of the emulsion. Accordingly, a variety of peptides, having different properties, may be used in various formulations and embodiments of the present invention. Similarly, nitric oxide may be added during or after the formulation of any phase or composition as described herein, e.g., by routine methods and those described herein, e.g., by bubbling nitric oxide gas through any phase, formulation, or composition, as described herein.

In another set of embodiments, the composition may also include one or more transdermal penetration enhancers. Examples of transdermal penetration enhancers include, but are not limited to, 1,3-dimethyl-2-imidazolidinone or 1,2-propanediol. Other examples include cationic, anionic, or nonionic surfactants (e.g., sodium dodecyl sulfate, polyoxamers, etc.); fatty acids and alcohols (e.g., ethanol, oleic acid, lauric acid, liposomes, etc.); anticholinergic agents (e.g., benzilonium bromide, oxyphenonium bromide); alkanones (e.g., n-heptane); amides (e.g., urea, N,N-dimethyl-m-toluamide); organic acids (e.g., citric acid); sulfoxides (e.g., dimethylsulfoxide); terpenes (e.g., cyclohexene); ureas; sugars; carbohydrates or other agents. The transdermal penetration enhancers can be present in any suitable amount within the composition. For example, at least about 10 wt %, at least about 20 wt %, at least about 30 wt %, at least about 40 wt %, or at least about 50 wt % of the composition may comprise one or more transdermal penetration enhancers. In some cases, no more than about 60 wt %, no more than about 50 wt %, no more than about 40 wt %, no more than about 30 wt %, no more than about 20 wt %, no more than about 10 wt %, no more than about 9 wt %, or no more than about 5 wt % of the composition comprises transdermal penetration enhancers. For example, the composition may have between about 0 wt % and about 5 wt % of one or more transdermal penetration enhancers.

In other embodiments, the composition may be modified in order to control depth of penetration. For example, in certain embodiments, the composition includes one or more polymers that act to reduce penetration depth of nitric oxide and/or peptide. Controlled depth of penetration may be important for indications where local administration is desired without systemic effects. Examples of transdermal penetration barrier polymers include, but are not limited to, silicone waxes, acrylate polymers, and dimethicone copolymers. In certain embodiments, a transdermal penetration barrier polymer is nonionic. A transdermal penetration barrier polymer can be present in any suitable amount within the composition. For example, at least about 10 wt %, at least about 20 wt %, at least about 30 wt %, at least about 40 wt %, or at least about 50 wt % of the composition may comprise one or more transdermal penetration barrier polymers. In some cases, no more than about 60 wt %, no more than about 50 wt %, no more than about 40 wt %, no more than about 30 wt %, no more than about 20 wt %, no more than about 10 wt %, no more than about 9 wt %, or no more than about 5 wt % of the composition comprises a transdermal penetration barrier polymer. For example, the composition may have between about 0 wt % and about 5 wt % of one or more transdermal penetration barrier polymers.

As a specific non-limiting example of one set of embodiments, a polyenylphosphatidylcholine comprises a certain material with the trade name NAT 8729, and optionally at least one polyglycol (polyhydric alcohol of a monomeric glycol such as polyethylene glycol 200, 300, 400, 600, 1,000, 1,450, 3,350, 4,000, 6,000, 8,000 and 20,000). The composition can also comprise a PPC-enriched phosphatidylcholine material that is present within the first or second phase, e.g., comprising nitric oxide, peptide, or both. The second phase may also comprise a surfactant such as a siloxylated polyether comprising dimethyl, methyl(propylpolyethylene oxide propylene oxide, acetate) siloxane commercially available from vendors such as Dow Corning (Dow Corning 190 surfactant) and lubricant such as silicone fluids containing low viscosity polydimethylsiloxane polymers, methylparaben (p-hydroxy benzoic acid methyl ester) commercially available from vendors such as Down Corning (Dow Corning 200 silicone fluid).

In some embodiments, various compositions of the invention are formulated to be substantially clear or substantially transparent. Transparency may be useful, for instance, for product acceptance in the marketplace, e.g., when applied to the skin of a subject. However, in other embodiments, the composition is not necessarily transparent. Certain substances can be useful in providing a substantially transparent composition, for example, fatty acid esters such as ascorbate palmitate or isopropyl palmitate. In one set of embodiments, the composition may be substantially transparent such that incident visible light (e.g., have wavelengths of between about 400 nm and about 700 nm) can be transmitted through 1 cm of the composition with a loss in intensity of no more than about 50%, about 60%, about 70%, about 80%, or about 90% relative to the incident light. In some embodiments, there may be no substantial difference in the wavelengths that are absorbed by the composition (i.e., white light passing through the composition appears white), although in other cases, there can be more absorption at various wavelengths (for example, such that white light passing through the composition may appear colored).

Other components may also be present within the composition, in accordance with certain embodiments of the invention. For example, the composition may include volatile organic fluids, fatty acids, volatile aromatic cyclic compounds, high molecular weight hydrocarbons, or the like.

In accordance with certain aspects of the invention, the composition may be prepared by mixing a first phase and a second phase together, then passing nitric oxide through the mixture. As discussed above, the second phase can comprise an emulsifier, or any other components discussed herein. The first phase may comprise a lecithin such as phosphatidylcholine and/or polyenylphosphatidylcholine, e.g., PPC-enriched phosphatidylcholine, for instance, as described herein. In some embodiments, other components are also mixed into the composition, before or after (or while) adding nitric oxide, for example, peptides, transdermal penetration enhancers, adjuvants, polyglycols (e.g., PEG and/or PPG), surfactants, lubricants, etc. as discussed herein. In some embodiments, however, nitric oxide may be passed through the first phase prior to mixing of the first phase with the second phase.

In one set of embodiments, after forming the mixture, nitric oxide can be passed into or through the mixture, for example, by blowing bubbles of nitric oxide through the mixture. Nitric oxide may be delivered into the mixture under pressures such as between about 3,000 Pa and about 15,000 Pa, between about 5,000 Pa and about 10,000 Pa, or between about 6,000 Pa and about 8,000 Pa, and/or temperatures such as between about 0° C. and about 50° C., between about 20° C. and about 35° C., or about 25° C. and about 30° C. However, higher or lower pressures also may be used in some embodiments as aspects of the invention are not limited in this respect.

In certain embodiments, the nitric oxide is bubbled through the mixture until the mixture begins to at least partially solidify. As an example, the viscosity of the mixture may increase to at least about 1,000 cP, at least about 2,000 cP, at least about 3,000 cP, at least about 5,000 cP, at least about 7,000 cP, at least about 10,000 cP, at least about 12,000 cP, at least about 15,000 cP, at least about 20,000 cP, at least about 30,000 cP, at least about 40,000 cP, at least about 50,000 cP, at least about 60,000 cP, at least about 70,000 cP, or at least about 80,000 cP. The nitric oxide can be passed through the mixture as pure nitric oxide, and/or with other gases (e.g., a noble gas, for example, argon). In some cases, a nitric oxide donor may be passed into the mixture, and therein, at least some of the nitric oxide donor can be converted into nitric oxide. In other embodiments, however, the final composition may have lower viscosities, for example, such that the composition is liquid, or could be sprayed onto the skin.

In one set of embodiments, the nitric oxide can be bubbled through the mixture to cause the viscosity of the mixture to increase. For example, the viscosity can increase until the mixture begins to form a gel, a cream, a lotion, an ointment, a solid "stick," or the like. A cream may be, for example, a semi-solid emulsion, e.g., comprising a first phase and a second phase. The first phase may be discontinuous (e.g., comprising small droplets or vesicles, such as is discussed herein) and the second phase may be continuous, or vice versa. In some cases, however, both the first phase and the second phase are co-continuous within the mixture.

In some embodiments of the invention, a composition may be prepared as discussed above, then diluted, e.g., with a diluent, to produce a final composition. For example, a "stock" composition may be initially prepared, e.g., having a relatively high nitric oxide and/or peptide concentration, then the stock composition diluted to produce a final composition, e.g., before use, before storage, before packaging, etc. In some embodiments, the diluent used may be a component as discussed herein (for example, forming at least a portion of the second phase), and the same or different materials than may be present in the initial composition may be used. The dilution ratio (amount of diluent added, relative to the initial composition) may be at least about 2, at least about 3, at least about 5, at least about 10, at least about 15, at least about 20, at least about 25, at least about 30, at least about 50, or at least about 100, or any other suitable factor.

A composition may be prepared and/or stored at any suitable temperature and under any suitable conditions. In some embodiments, for instance, a composition can be prepared and/or stored under limited or no oxygen conditions, as oxygen can adversely react with nitric oxide. The composition can also be prepared and/or stored under limited or no nitrogen and/or carbon dioxide, as both can also react adversely with nitric oxide. For instance, the composition may be prepared and/or stored in a sealed environment (e.g., stored in a sealed container). The sealed environment (e.g., container) can be at least substantially devoid of gas, and/or contains a gaseous mixture that excludes, or at least is depleted in, oxygen. In some embodiments, an environment depleted in oxygen may have less than about 20%, less than about 15%, less than about 10%, less than about 5%, about 1% or less, about 0.1% or less, about 0.01% or less, about 0.001% or less, oxygen (e.g., as a wt % or as molar % per volume). For example, the gaseous mixture may include a noble gas, such as argon, helium, neon, etc. In one set of embodiments, the container may comprise a multi-layered metallic and/or polymeric barrier, e.g., formed from Glaminate® (American Can Company). For instance, the container may have the shape of a tube. Thus, in certain embodiments, the container is substantially resistant to oxygen permeation, nitrogen permeation, and/or carbon dioxide permeation. In certain embodiments, the container is substantially watertight, for example, such that substantially no water is absorbed by the container, or such that no water is able to pass through the container even if the container is filled with water.

As previously discussed, nitric oxide can react with water, and thus, compositions described herein may be prepared and/or stored under conditions where substantially no water is present. For example, nitric oxide and/or a nitric oxide containing preparation described herein may be prepared and/or stored under relatively low relative humidities (e.g., less than about 50% RH, less than about 40% RH, less than about 30% RH, less than about 20% RH, or less than about 10% RH), and/or in the presence of a suitable desiccant, such as phosphorous pentoxide or silica gel.

In certain embodiments, the mixture may be mixed with or otherwise include adjunct ingredients, if applicable, and nitric oxide may be introduced to the mixture, e.g., bubbles of nitric oxide gas may be blown into the mixture until the mixture hardens to obtain the desired final composition. As a specific non-limiting example, a nitric oxide and/or peptide composition may be formed by preparing a non-liposome multilamellar liquid crystal phosphatidylcholine phase, for example, by providing a polyglycol, then introducing phosphatidyl choline into the glycol at room temperature to form a phosphatidylcholine solution. The phosphatidylcholine often comes as a solid (e.g., as a "brick" of material), and the phosphatidylcholine may be broken down into smaller pieces to aid in mixing, e.g., by "shaving" or grinding the phosphatidylcholine solid. The phosphatidylcholine solution is mixed until the phosphatidylcholine solution is substantially clear, then one may warm the phosphatidylcholine solution to 40° C., mill the warmed solution (i.e., low agitation after the initial mixing), combine siloxylated polyether and polydimethylsiloxane to form a fluid, add the fluid to the warmed solution and milling until the solution is clear, adding methyl paraben or other suitable lubricant to the solution and milling until the methyl paraben dissolves in the solution, warm water to 40° C. and adding the warmed water slowly to the solution, and then ceasing milling of the solution and "sweeping" the solution (e.g., with a sweep mixer) to cool to room temperature. Nitric oxide gas can then be bubbled or otherwise introduced into the solution while cooling the solution until the solution begins to harden or becomes stiff, e.g., having the consistency of a gel or a cream, such as previously described. In some cases, the resulting composition is sealed in a container, for example, as discussed herein. Any suitable container may be used, e.g., a tube or a bottle. In addition, the composition (e.g., within the container) may be stored at room temperature, or any other suitable temperature. For example, a composition of the invention may be stored at or below 80° C., e.g., at or below room temperature (about 25° C.) or in a refrigerator (e.g., at 4° C.) for extended period of storage, for instance, to prevent nitric oxide leakage or denaturing. In some cases, storage may extend for at least about a week, at least about 4 weeks, at least about 6 months, at least about a year, etc.

It is surprising that, according to some embodiments, nitric oxide and/or peptide not only can be entrapped in phosphatidylcholine or lecithin compositions such as those described herein, but also that such entrapped compositions may have a long shelf life, especially when refrigerated. No loss or reaction of nitric oxide, peptide, or both, is expected during extended refrigerated storage, at least under certain conditions. For instance, in certain embodiments, the composition may be stored at temperatures of less than about 80° C., less than about 70° C., less than about 60° C., less than about 50° C., less than about 40° C., less than about 30° C., less than about 25° C., less than about 20° C., less than about 15° C., less than about 10° C., less than about 5° C., less than about 0° C., etc., for extended periods of time, e.g., at least about a day, at least about a week, at least about 4 weeks, at least about 6 months, etc.

Without wishing to be bound by theory, it is believed that nitric oxide forms reversible physical bonds, similar to hydrogen bonds or van der Waals forces, with phosphatidylcholine or other lecithin molecules, e.g., containing one or more double bonds, which may allow nitric oxide to become entrapped and thereby remain intact for an extended period of time, e.g., during storage. These physical bonds, however, are believed to be not very stable, and may in some cases be easily broken up, for example, upon various physical agitations such as rubbing the composition against skin, thereby releasing the entrapped nitric oxide. While others have stabilized other substances or drugs within phosphatidylcholine or lecithin compositions or vesicles, for example, protein drugs such as insulin, it is surprising that a small, highly reactive molecule such as NO could similarly be stabilized, especially when it would have been expected that a molecule as small as NO would readily diffuse away from such compositions and/or would have reacted with water that is typically present within such compositions.

In some embodiments, it is believed that other species reactive with water could also be similarly stabilized, e.g., within a composition as herein described. Any species that ordinarily reacts with water could be stabilized within such compositions. Examples of such species include, but are not limited to, lithium, or drugs or polymers with labile bonds susceptible to hydrolysis, for instance, certain peptides, polysaccharides, polylactic acid, polyglycolic acid, etc.

In certain aspects of the invention, a composition such as those described herein can be administered to a subject, such as a human subject, by rubbing it on the skin of the subject, e.g., in areas located at or at least within the vicinity of a desired target area. Without wishing to be bound by any theory, it is believed that phosphatidylcholine provides or facilitates delivery of nitric oxide and/or peptide to the skin, and/or to tissues below the skin, allowing nitric oxide and/or peptide to be delivered to a target area. In some embodiments, the composition can be applied, by rubbing the composition topically against the skin, which allows the composition (or at least, nitric oxide and/or peptide) to be absorbed by the skin. The composition can be applied once, or more than once. For example, the composition may be administered at predetermined intervals. In some embodiments, for instance, the composition may be applied once per day, twice per day, 3 times per day, 4 times per day, once every other day, once every three days, once every four days, etc. The amount of nitric oxide and/or peptide necessary to bring about the therapeutic treatment is not fixed per se, and may depend upon factors such as the desired outcome, the type and severity the disease or condition, the form of nitric oxide and/or peptide, the concentration of nitric oxide and/or peptide present within the composition, etc.

Thus, another aspect of the invention provides methods of administering any composition such as discussed herein to a subject. When administered, the compositions of the invention are applied in a therapeutically effective, pharmaceutically acceptable amount as a pharmaceutically acceptable formulation. Any of the compositions of the present invention may be administered to the subject in a therapeutically effective dose. When administered to a subject, effective amounts will depend on the particular condition being treated and the desired outcome. A therapeutically effective dose may be determined by those of ordinary skill in the art, for instance, employing factors such as those described herein and using no more than routine experimentation. For example, in some cases a therapeutically effective dose is determined to be the dose necessary to promote hair growth or hair pigmentation in a subject so as to achieve a desirable look or appearance. In some aspects, a therapeutically effective dose is determined to be the dose necessary to promote hair growth as measured in terms hair density, hair diameter, hair growth rate, or anagen/telogen ratio, e.g., by methods described herein utilizing digital images of a subjects hair taken over time and analyzed by certain software (e.g., TRICHOSCAN®).

In certain embodiments of the invention, the administration of various compositions of the invention may be designed so as to result in sequential exposures to the composition over a certain time period, for example, hours, days, weeks, months, or years. This may be accomplished, for example, by repeated administrations of a composition of the invention by one or more of the methods described herein, or by a sustained or controlled release delivery system in which the composition is delivered over a prolonged period without repeated administrations. Administration of the composition using such a delivery system may be, for example, by a transdermal patch. Maintaining a substantially constant concentration of the composition may be preferred in some cases.

For certain chronic treatments or therapies, it is contemplated that a composition as discussed herein may be used to deliver nitric oxide and/or peptide to the skin at a relatively high concentration during an initial treatment, and the amount of nitric oxide and/or peptide may be lowered or "titrated" down to a relatively lower concentration maintenance dose or amount. A composition comprising nitric oxide and/or peptide, e.g., as described herein, can be used to promote vasodilation of blood vessels within and/or under the skin, and/or promote hair growth and/or hair pigmentation. As a specific example, a composition described herein may be used for certain treatments of hair loss and/or loss of hair pigmentation, e.g., baldness and/or greying of the hair. In some cases, gradual improvement may be observed with successive applications.

In some embodiments, an effective amount is an amount sufficient to have a measurable positive effect on blood flow and/or vasodilation, and/or a measurable negative effect on blood pressure. In some embodiments, the effect on blood flow and/or vasodilation is observed local to the site of topical application. In some embodiments, an effective amount is an amount sufficient to have a measurable effect on treatments of hair loss and/or loss of hair pigmentation, e.g., baldness and/or greying of the hair, or other treatments such as described herein.

The compositions described herein can be used in combination therapy with one or more additional therapeutic agents. For combination treatment with more than one active agent, where the active agents are in separate dosage formulations, the active agents may be administered separately or in conjunction. In addition, the administration of one element may be prior to, concurrent to, or subsequent to the administration of the other agent. In certain embodiments, the additional therapeutic agent is present in a provided composition in addition to nitric oxide and/or peptides. In other embodiments, the additional therapeutic agent is administered separately from the nitric oxide and/or peptide containing composition.

When co-administered with other agents, an "effective amount" of the second agent will depend on the type of drug used. Suitable dosages are known for approved agents and can be adjusted by the skilled artisan according to the condition of the subject, the type of condition(s) being treated and the amount of a compound described herein being used. In cases where no amount is expressly noted, an effective amount should be assumed. For example, compounds described herein can be administered to a subject in a dosage range from between about 0.01 to about 10,000 mg/kg body weight/day, about 0.01 to about 5000 mg/kg body weight/day, about 0.01 to about 3000 mg/kg body weight/day, about 0.01 to about 1000 mg/kg body weight/day, about 0.01 to about 500 mg/kg body weight/day, about 0.01 to about 300 mg/kg body weight/day, about 0.01 to about 100 mg/kg body weight/day.

In one set of embodiments, the dosage may be between about 0.01 mg and about 500 g, between about 0.01 mg and about 300 g, between about 0.01 mg and about 100 g, between about 0.01 mg and about 30 g, between about 0.01 mg and about 10 g, between about 0.01 mg and about 3 g, between about 0.01 mg and about 1 g, between about 0.01 mg and about 300 mg, between about 0.01 mg and about 100 mg, between about 0.01 mg and about 30 mg, between about 0.01 mg and about 10 mg, between about 0.01 mg and about 3 mg, between about 0.01 mg and about 1 mg, between about 0.01 mg and about 0.3 mg, or between about 0.01 mg and about 0.1 mg.

In certain embodiments, a nitric oxide and/or peptide containing composition as described herein, and the additional therapeutic agent are each administered in an effective amount (i.e., each in an amount which would be therapeutically effective if administered alone). In other embodiments, a nitric oxide and/or peptide containing composition as described herein, and the additional therapeutic agent are each administered in an amount which alone does not provide a therapeutic effect (a sub-therapeutic dose). In yet other embodiments, a nitric oxide and/or peptide containing composition as described herein can be administered in an effective amount, while the additional therapeutic agent is administered in a sub-therapeutic dose. In still other embodiments, a nitric oxide and/or peptide containing composition as described herein can be administered in a sub-therapeutic dose, while the additional therapeutic agent is administered in an effective amount.

As used herein, the terms "in combination" or "co-administration" can be used interchangeably to refer to the use of more than one therapy (e.g., one or more prophylactic and/or therapeutic agents). The use of the terms does not restrict the order in which therapies (e.g., prophylactic and/or therapeutic agents) are administered to a subject.

Co-administration encompasses administration of the first and second amounts of the compounds in an essentially simultaneous manner, such as in a single pharmaceutical composition, for example, capsule or tablet having a fixed ratio of first and second amounts, or in multiple, separate capsules or tablets for each. In addition, such co-administration also encompasses use of each compound in a sequential manner in either order. When co-administration involves the separate administration of the first amount of a composition as described herein, and a second amount of an additional therapeutic agent, the compounds are administered sufficiently close in time to have the desired therapeutic effect. For example, the period of time between each administration which can result in the desired therapeutic effect, can range from minutes to hours and can be determined taking into account the properties of each compound. For example, a composition as described herein, and the second therapeutic agent can be administered in any order within about 24 hours of each other, within about 16 hours of each other, within about 8 hours of each other, within about 4 hours of each other, within about 1 hour of each other or within about 30 minutes of each other.

More specifically, a first therapy (e.g., a prophylactic or therapeutic agent such as a composition described herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject.

In one set of embodiments, a composition such as is discussed herein may be applied to the skin of a subject, e.g., at any suitable location. The composition may be contacted using any suitable method. For example, the composition may be rubbed on, poured on, applied with an applicator (e.g., a gauze pad, a swab, a bandage, etc.), or the like. In some cases, the composition can be a liquid, a gel, a cream, a lotion, an ointment, a solid "stick," or the like, that can be applied to the skin by hand, for example, by rubbing or spraying.

Compared to other means of administration, the use of topical administration in certain embodiments of the present invention has various advantages, including one or more of the following. In some cases, administration of a composition and delivery of nitric oxide, peptide, or both as discussed herein is easier and more effective than other drug administration routes, for example, oral delivery. Unlike oral administration where a substantial amount of nitric oxide and/or peptide may be destroyed during the digestive process, nitric oxide, peptide, or both delivered topically is not exposed to the digestive tract. Topical application may also allow, in some instances, relatively steady delivery of nitric oxide, peptide, or both to the desired target area without the cyclic dosages typical of orally or parenterally administered drugs. In some embodiments, topical application may also avoid toxic side effects associated with sustained increased levels of nitric oxide and/or peptide typical of oral or parenteral administration.

Compared to other topical delivery systems that employ nitric oxide donors (an entity that is able to release nitric oxide, such as L-arginine, nitroglycerin, or amyl nitrite) as a nitric oxide source, various aspects of the present invention utilizing nitric oxide gas have several advantages, including one or more of the following. Nitric oxide can be released relatively quickly in some embodiments, because the release does not necessarily involve chemical transformations of nitric oxide donors to release nitric oxide. The concentration of nitric oxide can accumulate quickly upon topical administration, leading to good therapeutic effect in certain embodiments of the invention. Thus, for example, rapid nitric oxide delivery may provide quicker effect in addressing issues of hair loss than is possible with oral dosage forms of drugs such as finasteride. In other applications, it is expected that nitric oxide and/or peptides can be similarly delivered rapidly. In some embodiments, the release rate of nitric oxide, peptide, or both, can be controlled, for instance, by physical actions (e.g., by controlling how much of the composition is applied to the skin), in comparison to nitric oxide donors which release nitric oxide upon chemical stimulation. Moreover, certain embodiments of the present invention employ phosphatidylcholine, a component of cell membranes, as a carrier which improves the penetration and absorption of nitric oxide, peptides, or both into cells and tissues. Thus, certain compositions of the present invention will be non-toxic or biocompatible.

The compositions of the present invention may additionally comprise one or more adjunct ingredients, for instance, pharmaceutical drugs or skin care agents. For example, compositions of the invention may include adjuvants such as salts, buffering agents, diluents, excipients, chelating agents, fillers, drying agents, antioxidants, antimicrobials, preservatives, binding agents, bulking agents, silicas, solubilizers, or stabilizers. Non-limiting examples include species such as calcium carbonate, sodium carbonate, lactose, kaolin, calcium phosphate, or sodium phosphate; granulating and disintegrating agents such as corn starch or algenic acid; binding agents such as starch, gelatin or acacia; lubricating agents such as magnesium stearate, stearic acid, or talc; time-delay materials such as glycerol monostearate or glycerol distearate; suspending agents such as sodium carboxymethylcellulose, methylcellulose, hydroxypropylmethylcellulose, sodium alginate, polyvinylpyrrolidone; dispersing or wetting agents such as lecithin or other naturally-occurring phosphatides; thickening agents such as cetyl alcohol or beeswax; buffering agents such as acetic acid and salts thereof, citric acid and salts thereof, boric acid and salts thereof, or phosphoric acid and salts thereof; or preservatives such as benzalkonium chloride, chlorobutanol, parabens, or thimerosal. Suitable concentrations can be determined by those of ordinary skill in the art, using no more than routine experimentation. Those of ordinary skill in the art will know of other suitable formulation ingredients, or will be able to ascertain such, using only routine experimentation.

Preparations can include sterile aqueous or nonaqueous solutions, suspensions and emulsions, which can be isotonic with the blood of the subject in certain embodiments. Examples of nonaqueous solvents are polypropylene glycol, polyethylene glycol, vegetable oil such as olive oil, sesame oil, coconut oil, arachis oil, peanut oil, mineral oil, organic esters such as ethyl oleate, or fixed oils including synthetic mono or di-glycerides. Aqueous solvents include water, alcoholic/aqueous solutions, emulsions or suspensions, including saline and buffered media. Parenteral vehicles include sodium chloride solution, 1,3-butandiol, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents and inert gases and the like. Those of skill in the art can readily determine the various parameters for preparing and formulating the compositions of the invention without resort to undue experimentation.

In another aspect, the present invention is directed to a kit including one or more of the compositions discussed herein. A "kit," as used herein, typically defines a package or an assembly including one or more of the compositions of the invention, and/or other compositions associated with the invention, for example, as described herein. Each of the compositions of the kit may be provided in liquid form (e.g., in solution), or in solid form (e.g., a dried powder). In certain cases, some of the compositions may be constitutable or otherwise processable (e.g., to an active form), for example, by the addition of a suitable solvent or other species, which may or may not be provided with the kit. Examples of other compositions or components associated with the invention include, but are not limited to, solvents, surfactants, diluents, salts, buffers, chelating agents, fillers, antioxidants, binding agents, bulking agents, preservatives, drying agents, antimicrobials, needles, syringes, packaging materials, tubes, bottles, flasks, beakers, dishes, frits, filters, rings, clamps, wraps, patches, containers, and the like, for example, for using, administering, modifying, assembling, storing, packaging, preparing, mixing, diluting, and/or preserving the compositions components for a particular use, for example, to a sample and/or a subject.

A kit of the invention may, in some cases, include instructions in any form that are provided in connection with the compositions of the invention in such a manner that one of ordinary skill in the art would recognize that the instructions are to be associated with the compositions of the invention. For instance, the instructions may include instructions for the use, modification, mixing, diluting, preserving, administering, assembly, storage, packaging, and/or preparation of the composition and/or other compositions associated with the kit. In some cases, the instructions may also include instructions for the delivery and/or administration of the compositions, for example, for a particular use, e.g., to a sample and/or a subject. The instructions may be provided in any form recognizable by one of ordinary skill in the art as a suitable vehicle for containing such instructions, for example, written or published, verbal, audible (e.g., telephonic), digital, optical, visual (e.g., videotape, DVD, etc.) or electronic communications (including Internet or web-based communications), provided in any manner.

International Patent Application No. PCT/US2012/000151, filed Mar. 17, 2012, entitled "Topical Nitric Oxide Systems and Methods of Use Thereof," by Nicholas V. Perricone, et al., is incorporated herein by reference in its entirety. In addition, the following applications, each filed on Sep. 19, 2012, each by Nicholas V. Perricone, are hereby incorporated by reference in their entireties: "Systems and Methods for Treatment of Acne Vulgaris and Other Conditions with a Topical Nitric Oxide Delivery System" (U.S. patent application Ser. No. 13/623,008); "Treatment of Skin and Soft Tissue Infection with Nitric Oxide" (U.S. patent application Ser. No. 13/623,010); "Methods and Systems for Treatment of Inflammatory Dermatoses with Nitric Oxide" (U.S. patent application Ser. No. 13/623,014); "Prevention and Treatment of Cardiovascular Diseases using Systems and Methods for Transdermal Nitric Oxide Delivery" (U.S. patent application Ser. No. 13/623,018); "Treatment and Prevention of Learning and Memory Disorders" (U.S. patent application Ser. No. 13/623,022); "Methods and Compositions for Muscular or Neuromuscular Diseases" (U.S. patent application Ser. No. 13/622,998); "Compositions and Methods for Treatment of Osteoporosis and Other Indications" (U.S. patent application Ser. No. 13/623,004); "Techniques and Systems for Treatment of Neuropathic Pain and Other Indications" (U.S. patent application Ser. No. 13/623,027); and "Cancer Treatments and Compositions for Use Thereof" (U.S. patent application Ser. No. 13/622,989).

Additionally, the following U.S. patent applications, each filed on the same date as the earliest date to which the instant application claims priority, are hereby incorporated by reference in their entireties: "Systems and Methods for Delivery of Peptides"; "Treatment of Skin, Including Aging Skin, to Improve Appearance"; "Skin Tanning Using Peptides and Other Compositions"; "Topical Systems and Methods for Treating Sexual Dysfunction"; "Immune Modulation Using Peptides and Other Compositions"; "Cardiovascular Disease Treatment and Prevention"; "Wound Healing Using Topical Systems and Methods"; "Peptide Systems and Methods for Metabolic Conditions"; "Methods and Systems for Treating or Preventing Cancer"; "Compositions and Methods for Affecting Mood States"; "Improvement of Memory or Learning Using Peptide and Other Compositions"; and "Brain and Neural Treatments Comprising Peptides and Other Compositions."

The following examples are intended to illustrate certain embodiments of the present invention, but do not exemplify the full scope of the invention.

Example 1

This example illustrates one technique for preparing a composition in accordance with one embodiment of the invention. An accurate amount of a carrier (HNC 167-62) (see below) was introduced into a system. The carrier weight used in these experiments was approximately 250 g and the vessel size was 500 ml. The vessel was equipped with a mechanical stirrer, gas inlet, and gas outlet and was previously purged with argon for about an hour. The temperature of the carrier was kept at about 25-30° C. NO gas regulated at 5 psi (1 psi is about 6,900 Pa) and was then introduced at a controlled rate of about 1 bubble/s with continuous stirring. The color, consistency, and viscosity of the carrier did not appear to change if NO was bubbled for 30 minutes to 2 hours. After 6 hours, the weight of the carrier had increased by 0.15%, by 12 hours by 0.25%, and by 24 hours by 0.56%. These increases in weight were believed to be significant considering the relative small molecular weight of NO versus the carrier. Although there was a slight change in color during the experiment (the color changed to slightly more orange), IR spectrum analysis of the final product did not show any change versus the initial carrier, indicating no noticeable chemical change in the carrier. The carrier also can solidify upon cooling if the carrier is initially a solid at lower temperature. Accordingly, this example demonstrates that a composition containing NO can be prepared in accordance with one embodiment of the invention.

Example 2

In this example, six experiments were carried out to investigate the interaction of nitric oxide with three carriers (HNC 157-62, HNC 157-65, and HNC 157-69) as well as with 1,3-propanediol, using experimental conditions similar to that described for Example 1. In addition three experiments were performed to prepare carriers containing 800 ppm and 500 ppm nitric oxide. HNC 157-62 was formed of 65% Phospholipon-90G (American Lecithin Company), 18% isopropyl palmitate (Kraft Chemicals), 8% capric caprylic triglycerides (RITA Corp.), and 9% propanediol (Dupont). HNC 157-65 was formed of 65% Phospholipon-90G, 13% isopropyl palmitate, 14% capric caprylic triglycerides, 3% propanediol, and 5% dimethyl isosorbide (Croda). HNC 157-69 was formed from 65% Phospholipon-90G, 16% isopropyl palmitate, and 19% capric caprylic triglycerides.

The compositions were generally prepared as follows. Isopropyl palmitate, capric caprylic triglyceride, propanediol (for HNC 157-62 and HNC 157-65), and dimethyl isosorbide (for HNC 157-65) were mixed together and warmed to 40° C. Phospholipon-90G was then gradually added to this liquid mixture by mixing it. Phospholipon-90G is typically received as individual pellets, and is mixed into the solution until fully dissolved. The mixture was subsequently filtered through a sieve to remove any undissolved Phospholipon-90G.

Accordingly, the HNC carriers included 1,3-propanediol, Phospholipon-90G, isopropyl palmitate, capric and/or caporic triglycerides, and Arlasolve DMI (ICI America or Croda). Isopropyl palmitate, the capric and/or caporic triglycerides, and Arlasolve DMI are expected to be chemically inert towards nitric oxide, while the literature suggests that 1,2-propanediol and glycerol may be able to react with nitric oxide gas to form mononitrates. Accordingly, it would be expected that 1,3-propanediol may also react with NO to form mononitrates:

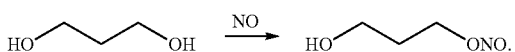

In addition, Phospholipon-90G is derived from soybean and contains esters of unsaturated fatty acids such as oleic, linoleic, and linolenic acids, and thus, the unsaturated fatty acid part of Phospholipon-90G would react with nitric oxide to lead to a variety of nitrated products.

Each carrier was taken in a 500 mL three necked flask equipped with a mechanical stirrer, gas inlet and a gas outlet. The system was purged with argon for one hour at room temperature (25° C.). Then nitric oxide gas was bubbled into the system. Then, nitric oxide gas was bubbled through carrier for stipulated amount of time. The changes in weight and color were noted. The details of individual experiments were as follows.

Experiment 1. The carrier was HNC 157-62. Nitric oxide gas was bubbled for 24 hours at 25° C. The initial weight of carrier was 168.53 g., and the final weight was 169.48 g. The net weight gained was 0.95 g and the percentage weight gain was 0.56%.

Experiment 2. The carrier used was HNC 157-62. Nitric oxide gas was bubbled for 48 hours at 25° C. The initial weight of carrier was 171.31 g., and the final weight was 174.21 g. The net weight gained was 2.90G and the percentage weight gain was 1.69%.

Experiment 3. In order to differentiate between chemical reaction vs. physical absorption, the above reaction mixtures were heated at 55-60° C. for four hours. Minimal loss of weight was observed (~200 mg), indicating no loss of absorbed nitric oxide gas. However, more intense orange color developed during this process, indicating some decomposition of the nitrites formed.

Experiment 4. The carrier used was HNC 157-65. Nitric oxide gas was bubbled for 24 hours at 25° C. The initial weight of carrier was 171.66 g., and the final weight was 172.98 g. The net weight gained was 1.32 g and percentage weight gain was 0.77%.

Experiment 5. The carrier used was HNC 157-69 (same as HNC 157-62, except it had no 1,3-propanediol). Nitric oxide gas was bubbled for 40 hours at 25° C. The initial weight of carrier was 171.02 g., and the final weight was 171.97 g. The net weight gained was 0.95 g and the percentage weight gain was 0.56%.

Experiment 6. Nitric oxide gas was bubbled through 1,3-propanediol (neat) for 40 hours at 25° C. The initial weight of the 1,3-propanediol was 178.81 g., and the final weight was 178.97 g. The net weight gained was 0.16 g and the percentage weight gain was 0.09%.

Experiment 7. For preparation of 800 ppm NO, the carrier used was HNC 157-62. Nitric oxide gas was bubbled for 2 hours at 25° C. The initial weight of carrier was 238.16 g., and the final weight was 238.35 g. The net weight gained was 0.19 g and the percentage weight gain 0.0798% (~800 ppm). See entry 5 in Table 1.

Experiment 8. For preparation of 500 ppm NO, the carrier used was HNC 157-65. Nitric oxide gas was bubbled for 2 hours at 25° C. The initial weight of carrier was 250.37 g., and the final weight was 250.50 g. The net weight gained was 0.13 g and the percentage weight gain was 0.0519% (~500 ppm). See entry 6 in Table 1.

Experiment 9. For preparation of 800 ppm NO, the carrier used was HNC 157-62. Nitric oxide gas was bubbled for 15 min at 25° C. The initial weight of carrier was 252.24 g., and the final weight was 252.45 g. The net weight gained was 0.21 g and the percentage weight gain 0.083% (~800 ppm).

These experiments were conducted with carriers the HNC 157-62, HNC 157-65, HNC 157-69, and 1,3-propanediol.

As described above and in Table 1, weight gains ranging from 0.5% to 1.7% were observed when nitric oxide gas was passed through the carriers. In order to determine the nature of interaction between nitric oxide and carrier, the carrier was heated after nitric oxide absorption at 60° C. for four hours. Practically no loss of weight was observed, which indicated that the nitric oxide gas reacted chemically with the carriers (entries 1-4 in Table 1).

In order to investigate the reactivity of 1,3-propanediol with nitric oxide, nitric oxide absorption was studied using (a) HNC 157-69, which did not contain 1,3-propanediol, and (b) 1,3-propanediol by itself. HNC 157-69 gained 0.95 g or 0.56% weight, much lower compared to its 1,3-propanediol containing analog HNC 157-62, which showed 1.69% weight gain (entries 2 and 5 of Table 1). 1,3-propanediol itself, surprisingly, showed only negligible, if any, weight gain when NO was passed through it (entry 6 in Table 1). Thus, under experimental conditions, 1,3-propanediol did not react with nitric oxide.

Two samples were also prepared containing 800 ppm NO (from carrier HNC 157-62) and one sample containing 500 ppm NO (from carrier HNC 157-65) (entries 7-9 in Table 1). The IR spectra of the carriers did not show any additional bands after the reaction, possibly because of low amounts of nitrites and/or overlap with the carrier complex bands.

Mass spectral studies of the carrier HNC 157-62 and HNC 157-62 containing NO indicated that there was an increase in the intensity of the peak at m/e 104 in NO-containing carrier, compared to carrier without NO. The peak at m/e 104 was believed to be due to choline cation ($C_5H_{14}NO$). Phospholipon-90G may contain some free choline, and hence presence of the peak at 104 in the mass spectrum of the carrier was not surprising. However, the increase in the amount of choline after passage of NO was somewhat unexpected, although it is believed that nitric oxide catalyzes similar dephosphorylation of Phospholipon-90G releasing choline.

In conclusion, an increase in weight (0.56 to 1.69%) was observed when nitric oxide gas was passed through the carriers. 1,3-propanediol failed to gain any significant weight when nitric oxide was passed through it. HNC 157-69 (devoid of 1,3-propanediol) gained only 0.56% weight compared to 1.69% by its 1,3-propanediol containing analog HNC 157-62. The mass spectra of HNC 157-62 before and after passing NO indicated that the peak corresponding to choline at m/e 104 increased after the passage of NO, which suggests that phospholipon-90G may undergo NO-catalyzed dephosphorylation.

TABLE 1

| Expt. No. | Carrier | Initial wt. g. | Final wt. g. | Time hr | Temp. °C. | Wt. Gain g | % Wt. gain |
|---|---|---|---|---|---|---|---|
| 1 | HNC 157-62 | 168.53 | 169.48 | 24 | 25 | 0.95 | 0.56 |
| 2 | HNC 157-62 | 171.31 | 174.21 | 48 | 25 | 2.90 | 1.69 |
| 3 | HNC 157-62 | 174.21* | 174.01 | 4 | 60 | −0.20 | −0.11 |
| 4 | HNC 157-65 | 171.66 | 172.98 | 24 | 25 | 1.32 | 0.77 |
| 5 | HNC 157-69 | 171.02 | 171.97 | 40 | 25 | 0.95 | 0.56 |
| 6 | 1,3-Propanediol | 178.81 | 178.97 | 40 | 25 | 0.16 | 0.09 |
| 7 | HNC 157-62 | 238.16 | 238.35 | 2 | 25 | 0.19 | 0.0798 (~800 ppm) |
| 8 | HNC 157-65 | 250.37 | 250.50 | 2 | 25 | 0.13 | 0.0519 (~500 ppm) |
| 9 | HNC 157-62 | 252.24 | 252.45 | 0.25 | 25 | 0.21 | 0.0833 (~800 ppm) |

Example 3

This example illustrates non-invasive blood pressure measurements in mice using a composition in accordance with one embodiment of the invention.

Blood pressure in mice may be measured using blood volume changes in the mouse tail. Mice with normal tails (no clipping or short) were used in this study. Ages varied between 8 weeks and 24 weeks. This procedure uses the CODA non-invasive blood pressure system available from Kent Scientific (Torrington, Conn.) Mice weighing approximately 25 grams were restrained in plastic cylindrical housing with a nose come allowing the nose to protrude. Two tail cuffs provided occlusion and measurements. The O-cuff provided period occlusion while the VPR cuff provides volume-pressure recordings. The occlusion pressure and the recorded pressure were controlled automatically by the computer software.

Each measurement had 10 acclimation cycles and 20 measurement cycles once daily depending on the experimental parameters. The average blood pressure of male mice made over time was 136/88. In this study, blood pressure measurements of the control (base) mice and the test (treated) mice were made and averaged over a period of three days. The test composition comprised 800 ppm nitric oxide, which was applied over the upper back of the animal in a quantity that exceeded 50 mg. The blood pressures were recorded after each application and over 1 hour. The following results were obtained.

TABLE 2

Average Blood Pressure Reading

| Post Application | Control (Base) Product | Test (Treated) NO 800 ppm |
|---|---|---|
| Time 0 | 167/123 | 140/91 |
| 1 Hour | 170/128 | 115/69 |

This study shows that the application of the test product is capable of reducing the blood pressure in a mouse to a significantly lower value.

Example 4

This example illustrates capillary blood flow measurements in humans using a composition similar to the ones described in the above examples.

Microcirculation properties of the skin were measured before and after application of a test product with nitric oxide. Measurements were made using a Moor® Laser Doppler instrument. Measurements were made at Day 1 before and immediately, 5 and 15 minutes after treatment.

The study participants were healthy females aged 30 to 55 years. They were in good health as determined by the medical history and were not taking any prescription medications. The test product was labeled as 800 ppm NO (nitric oxide). The study participants had 100 mg of the test product applied in a 2×2 sq. inch area on the forearm.

Laser Doppler was performed to measure increased stimulation of the micro-capillary blood flow to skin. The microcirculation of the skin reflects the perfusion of the skin and the underlying tissue. The laser Doppler technique is the standard method to obtain dynamic measurement of capillary blood flow in clinical evaluation. Measurements can be made relatively rapidly and simultaneously at sites. In addition, temperature measurements may also be made at the same time.

A Moor Instruments DRT4 Laser Doppler Blood Flow Monitor (Devon, England) was used. The laser Doppler technique measures blood flow in the microcapillaries of the skin that are close to the skin surface and the blood flow in underlying arterioles and venules that help to regulate skin temperature. There are several parameter used to describe blood flow measured by this laser Doppler technique. These measurement parameters are defined by Moor Instruments Inc. and are listed below.

Flux: This parameter is related to the product of average speed and concentration of moving red blood cells in the tissue sample volume. It is the parameter most widely reported in Laser Doppler publication.

Conc: This parameter gives an indication of the number of moving red blood cells in the tissue sample volume.

Speed: This parameter gives an indication of the average speed of red blood cells moving in the tissue sample volume.

Temp: This is the probe temperature and where there is good thermal conduction between probe and tissue it reaches tissue temperature.

Because of the nature of blood flow in the capillaries and other small blood vessels, absolute flow units such as ml/minute cannot be expressed. Therefore, arbitrary units are used. Blood flow changes are defined as the percentage change from the baseline of these arbitrary units.

The procedure was as follows. The laser Doppler probe was attached onto the volar forearm. Control untreated skin readings (Baseline) were obtained for 15 minutes. The test product was then applied in the designated 2×2 sq. inch area and rubbed into the skin. Readings were obtained for 15 minutes.

The areas not used for evaluation include the first 15 seconds after starting data collection. Four 10 second areas in the baseline and test readings at each time point were randomly selected to obtain the mean averages which were then used in further analysis of the data.

The averaged data was compiled from the 4 study participants and the laser Doppler results are provided in FIG. 1. There was a significant difference observed in the control untreated skin and the skin treated with 800 ppm nitric oxide up to 15 minutes after application. The applied nitric oxide had an effect on the micro circulation of the skin at the applied level (100 mg in a 2×2 sq. inch area). The topical test product is capable of passing through the skin and affecting the microcirculation of the skin.

Example 5

This example illustrates delivery of nitric oxide formulations similar to those discussed herein in humans. In these studies, laser Doppler studies were performed on three human female subjects. As discussed below, all of the studies showed positive results consistent with a physiological effect of nitric oxide applied to the skin, passing through the skin and affecting the capillary circulation. The formulations used produce positive, almost immediate results when applied to the skin which, in these studies, was manifested by vasodilatation of the cutaneous vascular system.

While nitric oxide has many physiological effects, the purpose of these studies was to measure physiological effects that would be relatively easy to determine, and which would be noninvasive. Laser Doppler was selected for these studies because laser Doppler has a relatively large database that indicates that it is effective in determining an increase in microcirculation, i.e., circulation within the capillary bed immediately under the epidermal layer in the skin. Nitric oxide is capable of violating the capillary bed, and thus, laser Doppler was selected.

The formulation used in these studies contained nitric oxide dispersed in a lipid matrix. The nitric oxide was dispersed in the matrix and does not appear to be dissolved but remained intact, i.e., it appeared to diffuse into the skin as a molecule of nitric oxide rather than as atomic components or ions. Nitric oxide is a very rapid acting molecule, and these studies used a system that employed laser Doppler with a covered chamber. The formulation was placed into the chamber and then attached to the skin by an adhesive layer on the covering. This provided a stable measuring device as determined by multiple normal evaluations of the capillary blood flow without treatment of nitric oxide.

A known positive control, methyl nicotinate, was applied to the skin at a concentration of 1/10% in alcohol. There was a rapid response typical of the vasodilator. The vascular dynamics are such that when the blood vessels dilate physical parameters follow Bernoulli's law. This states that as one increases the diameter of a tube containing a liquid to flow will increase but the pressure and the speed of the liquid will decrease. The laser Doppler device accurately measured these parameters.

When nitric oxide was applied to the forearm of three human female subjects, it was observed that there was an immediate effect on the blood flow as soon as the formulation was applied. The speed of blood flow decreased, and the effects lasted over 15 minutes. There was no erythema and no discomfort to the subjects that was observed.

Thus, these studies showed that the nitric oxide in the lipid matrix when applied topically to the forearm, was able to penetrate the skin very rapidly and to interact with the underlying tissues. This is evidenced by the observation of vascular dilatation without erythema. Accordingly, it can be concluded from these studies that the formulation containing nitric oxide was effective in delivering nitric oxide through the skin in a physiologically active state.

In these studies, the participants were healthy females aged 30 to 55 years. They were in good health as determined by the medical history and were not taking any prescription medications. All study participants read and signed the informed consent statement prior to any study procedures being performed.

The test product was labeled as 10,000 ppm NO (nitric oxide). The study participants had 100 mg of the test product applied in a closed Hilltop chamber on the forearm.

Laser Doppler was performed to measure increased stimulation of the micro-capillary blood flow to skin. The microcirculation of the skin reflected the perfusion of the skin and the underlying tissue. Laser Doppler is a standard method to obtain dynamic measurement of capillary blood flow in clinical evaluation. Measurements can be made relatively rapidly and simultaneously at sites. In addition, temperature measurements may also be made at the same time.

A Moor Instruments DRT4 Laser Doppler Blood Flow Monitor (Devon, England) was used in these studies. The laser Doppler technique measured blood flow in the microcapillaries of the skin that are close to the skin surface and the blood flow in underlying arterioles and venules that help to regulate skin temperature. Because of the nature of blood flow in the capillaries and other small blood vessels, it is difficult to determine absolute flow units such as ml/minute. Therefore, arbitrary units were used in these experiments to determine relative changes. Blood flow changes were accordingly defined as the percentage change from the baseline using the arbitrary units.

Data was compiled from the three study participants and the laser Doppler studies and averaged. It observed that there was a significant difference observed in the control untreated skin and the skin treated with 10,000 ppm nitric oxide up to 15 minutes after application. The applied nitric oxide had an effect on the microcirculation of the skin at the applied level (100 mg in a lipid matrix). The formulation was determined to be capable of passing through the skin and affecting the microcirculation of the skin.

Example 6

This example illustrates a protocol used for determining the amount of nitric oxide released from various compositions of the present invention. The protocol is generally performed as follows:

1) Samples (within HNC carriers described herein) were maintained at either 4° C. or −20° C. until analyzed.

2) One at a time and before they were opened, samples were warmed to 37° C. (dry bath) in a controlled atmosphere of 1% $O_2$. They were opened and 150 microliters was removed and placed into 1.35 mL of PBS (pH 7.4, 25° C. and equilibrated to 13 micromolar $O_2$) in a small glass screw-cap vial minimizing headspace.

3) The vials were then subjected to 15 s of vortex agitation, caps opened and 1 mL quickly removed and immediately injected into a Sievers Nitric Oxide Analyzer reaction chamber containing 4 mL of deionized and distilled $H_2O$ equilibrated at 0% $O_2$ by a $N_2$ flow through gas and maintained at 37° C. by flow-through water jacket.

4) Peaks were analyzed by comparing values to a standard curve generated by injecting various concentrations of the NO donor 1-(hydroxy-NNO-azoxy)-L-proline (PROLI-NONOate). To standardize among samples, the area under the curve from 0 to 4 min was used for concentration determinations are expressed in moles of NO and have been corrected for the 2 dilutions (50×). As such, these values equal moles of NO/150 microliter matrix.

5) The authenticity of NO formation was validated by injecting 50 mM of the NO spin trap 2-(4-carboxyphenyl)-4,5-dihydro-4,4,5,5-tetramethyl-1H-imidazolyl-1-oxy-3-oxide (cPTIO) or by injecting sample into the reaction chamber containing 50 mM cPTIO and observing the absence of signal.

6) For each sample, the area under the curve from t=0 to t=4 min was calculated for concentration determinations. Calculations represent only the amount of NO released during this 4 min time span and thus do not represent the total amount of NO contained in the volume of matrix assessed (150 microliters). For each vial 3-5 independent determinations were performed (this means each injection represents removal of 150 microliters of matrix from the labeled vial, dilution in PBS and injection. As such, these were completely independent measurements from beginning to end.

TABLE 3

| Sample ID | Mean (millimoles NO) | Std Dev |
|---|---|---|
| 1000 | 11.4 | 1.55 |
| 4000 | 60.7 | 1.70 |
| 7000 | 72.1 | 11.9 |
| 10000 | 127.9 | 11.3 |

In this table, the Sample ID numbers correspond to the amount of nitric oxide, in ppm, that was formulated in the composition (sample) tested.

Based on these results, the compositions tested here appeared to be effective in entrapping nitric oxide gas, and are effective in releasing the trapped gas in a measureable and significant way.

Example 7

This example illustrates techniques for preparing compositions in accordance with one or more embodiments of the invention. Specifically, four formulations suitable as peptide and nitric oxide carriers are provided: two four-phase formulations (HNC 156-43, HNC 156-50), and two single-phase formulations (HNC 156-47, HNC 159-136).

HNC 156-43

This formulation was formed of: 77.7% water, 6.0% Phospholipon-90G (American Lecithin Company), 0.10% EDTA-$Na_2$ (Sigma), 0.1% citric acid, 5.0% isopropyl palmitate (IPP, Kraft Chemicals), 5.0% Promulgen-D (Lubrizol), 3.0% Arlacel-165 (Croda), 1.0% cetearyl alcohol 50/50, 0.5% Dow Corning Fluid 200-10 CST, 0.1% Tocotrienol-50C (Carotech), 0.5% Optiphen Plus (Lotioncrafter), and 1.0% Seppitonic M3 (Seppic).

The individual ingredients were divided between four phases as follows:
Phase 1: water, Phospholipon-90G, EDTA-$Na_2$, citric acid.
Phase 2: IPP, Promulgen-D, Arlacel-165, cetearyl alcohol 50/50, Dow Corning Fluid 200-10 CST, Tocotrienol-50C.
Phase 3: Optiphen Plus.
Phase 4: Seppitonic M3.

HNC 156-50

This formulation was formed of: 78.3% water, 10.0% Phospholipon-90G (American Lecithin Company), 0.10% EDTA-$Na_2$ (Sigma), 0.2% sodium hyaluronate (1% solution), 3.0% isopropyl palmitate (IPP, Kraft Chemicals), 3.0% Promulgen-D (Lubrizol), 4.0% Arlacel-165 (Croda), 0.7% cetearyl alcohol 50/50, 0.5% Optiphen Plus (Lotioncrafter), and 0.2% dimethylethanolamine (DMAE, Sigma).

The individual ingredients were divided between four phases as follows:
Phase 1: water, Phospholipon-90G, EDTA-$Na_2$, sodium hyaluronate.
Phase 2: IPP, Promulgen-D, Arlacel-165, cetearyl alcohol 50/50.
Phase 3: Optiphen Plus.
Phase 4: DMAE.

The four-phase compositions were generally prepared as follows: Phases 1 and 2 were heated to 60° C., added and mixed together, then allowed to cool to 48° C., at which point Phase 3 was added and mixed. The mixture was then allowed to cool to 38° C., at which point phase 4 was added and mixed.

HNC 156-47

This formulation was formed of: 47% water, 5.0% PEG-200 (Sigma), 45% Phospholipon-90G (American Lecithin Company), 1.0% benzyl alcohol, and 2.0% ethyl alcohol.

HNC 159-136

This formulation was formed of: 65% Phospholipon-90G (American Lecithin Company), 18.0% isopropyl palmitate (IPP, Kraft Chemicals), 8% capric caprylic triglycerides (RITA Corp.), and 9% propanediol (Dupont).

Any of the above compositions are effective as carriers for peptides and nitric oxide. For example, the TRH peptide was shown to be effectively carried by each of the above formulations at a TRH concentration of 5.0 mg/cc.

Example 8

This example illustrates delivery of nitric oxide formulations to five human subjects, using procedures and formulations similar to those discussed in Example 5. Each person served as their own control for the testing. A Moor Instruments Laser Doppler was used to determine circulation. All of these studies showed positive results consistent with a physiological effect of nitric oxide applied to the skin, passing through the skin and affecting the capillary circulation. The formulations used produce positive, almost immediate results when applied to the skin which, in these studies, was manifested by vasodilatation of the cutaneous vascular system.

For each subject, the following creams were applied: a negative control formulation (containing no NO), 0.010 gram of a 10,000 ppm NO formulation, 0.020 gram of a 10,000 ppm NO formulation, and a positive control formulation containing 0.1% methyl nicotinate. The formulations were prepared using procedures similar to those discussed in Example 1.

When nitric oxide was applied to the forearm of the subjects, it was observed that there was an immediate effect on the blood flow as soon as the formulation was applied. The speed of blood flow decreased, and the effects lasted over 15 minutes. There was no erythema and no discomfort to the subjects that was observed.

Data was compiled from the study participants and the laser Doppler studies and averaged. It observed that there was a significant difference observed in the control untreated skin (where no detectable vasodilation was observed), and the treatments involving 0.010 g of NO, 0.020 g of NO, and methyl nicotinate. For all three treatments, vasodilatation was observed, with somewhat greater vasodilatation for the 0.010 g formulation over the 0.02 g formulation. In addition, the amount of vasodilatation observed for the 0.01 g formulation of NO was generally similar to the amount of vasodilatation observed for methyl nicotinate.

Accordingly, these data demonstrate that NO as applied in a cream to the skin is able to penetrate the skin and affect bloodflow beneath the skin.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method, comprising:
   administering, to the skin and/or hair of a subject, a composition comprising an effective amount of thyrotropin-releasing hormone (TRH) and molecular nitric oxide to increase hair growth, and a carrier having a phosphatidylcholine component entrapping the molecular nitric oxide, wherein the molecular nitric oxide is present within the carrier as a gas or bound by hydrogen bonds or van der Waals forces, wherein the composition is stable at room temperature.

2. The method of claim 1, comprising administering the composition to the skin or hair of the head of the subject.

3. The method of claim 1, wherein the subject has greying hair.

4. The method of claim 1, wherein the subject has thinning hair.

5. The method of claim 1, wherein the subject has baldness.

6. The method of claim 1, wherein the subject has androgenic alopecia.

7. The method of claim 1, wherein the phosphatidylcholine carrier stabilizes the nitric oxide at a temperature at or lower than 80° C.

8. The method of claim 1, wherein the composition comprises a liquid crystal structure comprising the phosphatidylcholine.

9. The method of claim 8, wherein at least a portion of the liquid crystal structure is multilamellar.

10. A method, comprising contacting the skin and/or hair of a subject with a composition comprising:
an emulsion comprising a first phase comprising TRH, molecular nitric oxide, and lecithin, and a second phase comprising an emulsifier, wherein the lecithin is present at least about 0.25% by weight of the composition, wherein the first phase comprises no more than about 250 ppm of water by weight of the composition, and wherein the molecular nitric oxide is present within the emulsion as a gas or bound by hydrogen bonds or van der Waals forces to the lecithin.

11. The method of claim 10, comprising administering the composition to the skin or hair of the head of the subject.

12. The method of claim 10, wherein the subject has greying hair.

13. The method of claim 10, wherein the subject has thinning hair.

14. The method of claim 10, wherein the subject has baldness.

15. The method of claim 10, wherein the subject has androgenic alopecia.

16. The method of claim 10, wherein the first phase forms discrete vesicles contained within the second phase.

17. The method of claim 16, wherein the first phase forms liposomes contained within the second phase.

18. The method of claim 17, wherein the first phase forms multilamellar liposomes contained within the second phase.

19. The method of claim 10, wherein the nitric oxide is present at least about 0.5% by weight of the composition without nitric oxide.

20. The method of claim 10, wherein at least some of the nitric oxide is present within the first phase bound to phosphatidylcholine.

21. The method of claim 10, wherein the lecithin comprises a phosphatidylcholine.

22. The method of claim 21, wherein at least some of the phosphatidylcholine comprises a polyenylphosphatidylcholine.

23. The method of claim 10, wherein the first phase comprises a fatty acid ester.

24. A method, comprising:
administering, topically to the skin of a subject, a composition comprising an effective amount of thyrotropin-releasing hormone (TRH) molecular nitric oxide and phosphatidylcholine to increase hair growth, wherein the composition is a cream, a gel, a lotion, or an ointment, and wherein the composition comprises no more than about 250 ppm of water by weight of the composition.

25. The method of claim 24, comprising administering the composition to the skin or hair of the head of the subject.

26. The method of claim 24, wherein the subject has thinning hair or baldness.

27. The method of claim 24, wherein the subject has androgenic alopecia.

28. The method of claim 24, wherein the composition comprises a liquid crystal structure comprising the phosphatidylcholine.

29. The method of claim 28, wherein at least a portion of the liquid crystal structure is multilamellar.

30. The method of claim 24, wherein at least some of the phosphatidylcholine comprises a polyenylphosphatidylcholine.

31. The method of claim 24, wherein the composition is a cream.

* * * * *